United States Patent
Mirghasemi et al.

(10) Patent No.: US 9,962,204 B2
(45) Date of Patent: May 8, 2018

(54) MODULAR BONE PLATE

(71) Applicants: Seyed Alireza Mirghasemi, Tehran (IR); Narges Rahimigabaran, Tehran (IR)

(72) Inventors: Seyed Alireza Mirghasemi, Tehran (IR); Narges Rahimigabaran, Tehran (IR)

( * ) Notice: Subject to any disclaimer, the term of this patent is extended or adjusted under 35 U.S.C. 154(b) by 56 days.

(21) Appl. No.: 14/684,379

(22) Filed: Apr. 11, 2015

(65) Prior Publication Data
US 2015/0289910 A1  Oct. 15, 2015

Related U.S. Application Data

(60) Provisional application No. 61/978,841, filed on Apr. 12, 2014, provisional application No. 61/984,748, filed on Apr. 26, 2014.

(51) Int. Cl.
*A61B 17/80* (2006.01)

(52) U.S. Cl.
CPC .......... *A61B 17/8014* (2013.01); *A61B 17/80* (2013.01); *A61B 17/808* (2013.01)

(58) Field of Classification Search
CPC ....................................... A61B 17/80–17/8095
See application file for complete search history.

(56) References Cited

U.S. PATENT DOCUMENTS

| | | | | |
|---|---|---|---|---|
| 2,486,303 A * | 10/1949 | Longfellow | ........... | A61B 17/80 606/71 |
| 3,528,085 A * | 9/1970 | Walker, Jr. | ......... | A61B 17/8014 52/848 |
| 4,957,496 A * | 9/1990 | Schmidt | ............. | A61B 17/8014 606/70 |
| 5,415,660 A * | 5/1995 | Campbell | .......... | A61B 17/7216 606/62 |
| 5,827,286 A * | 10/1998 | Incavo | ............... | A61B 17/8009 606/282 |
| 5,885,284 A * | 3/1999 | Errico | ................. | A61B 17/7052 606/252 |
| 6,645,208 B2 * | 11/2003 | Apfelbaum | ............ | A61B 17/80 606/281 |
| 6,932,820 B2 * | 8/2005 | Osman | ............... | A61B 17/7059 606/282 |
| 7,186,254 B2 * | 3/2007 | Dinh | .................. | A61B 17/7059 606/70 |
| 7,537,596 B2 | 5/2009 | Jensen | | |
| 7,635,365 B2 | 12/2009 | Ellis et al. | | |
| 7,635,366 B2 * | 12/2009 | Abdou | ............... | A61B 17/7059 606/71 |
| 7,785,355 B2 | 8/2010 | Mohr et al. | | |

(Continued)

FOREIGN PATENT DOCUMENTS

| | | | | |
|---|---|---|---|---|
| FR | 2828643 A1 * | 2/2003 | ......... | A61B 17/8023 |
| WO | WO 03071966 A1 * | 9/2003 | ......... | A61B 17/7059 |

*Primary Examiner* — Zade Coley

(57) ABSTRACT

Embodiments of present invention include modular bone plate systems and various methods of bone fixation using the same. The system makes available to the practitioner an array of plates, screws and pins with different sizes, curves, and functions to overcome complication of the procedure with minimal rework and soft/hard tissue intervention, treat osteoporotic bones and articular fracture to name a few.

10 Claims, 16 Drawing Sheets

(56) References Cited

U.S. PATENT DOCUMENTS

| | | | | |
|---|---|---|---|---|
| 8,083,781 B2* | 12/2011 | Reimels | A61B 17/8004 606/282 |
| 8,177,819 B2 | 5/2012 | Huebner et al. | |
| 8,328,853 B2* | 12/2012 | Ibrahim | A61B 17/7059 606/279 |
| 8,357,181 B2* | 1/2013 | Lange | A61B 17/7065 606/248 |
| 8,388,663 B2* | 3/2013 | Bush, Jr. | A61B 17/7059 606/282 |
| 8,636,738 B2* | 1/2014 | McClintock | A61B 17/1728 606/280 |
| 9,486,250 B2* | 11/2016 | Altarac | A61B 17/7059 |
| 2003/0212399 A1* | 11/2003 | Dinh | A61B 17/7059 606/71 |
| 2005/0010227 A1* | 1/2005 | Paul | A61B 17/7059 606/71 |
| 2007/0162021 A1* | 7/2007 | Dinh | A61B 17/7059 606/86 A |
| 2008/0065070 A1* | 3/2008 | Freid | A61B 17/1728 606/279 |
| 2009/0069851 A1* | 3/2009 | Gillard | A61B 17/1684 606/280 |
| 2010/0082029 A1* | 4/2010 | Ibrahim | A61B 17/7059 606/71 |
| 2010/0234888 A1* | 9/2010 | McClintock | A61B 17/1728 606/246 |
| 2013/0165934 A1* | 6/2013 | Ibrahim | A61B 17/7059 606/71 |
| 2015/0216570 A1* | 8/2015 | Hess | A61B 17/8009 606/70 |

* cited by examiner

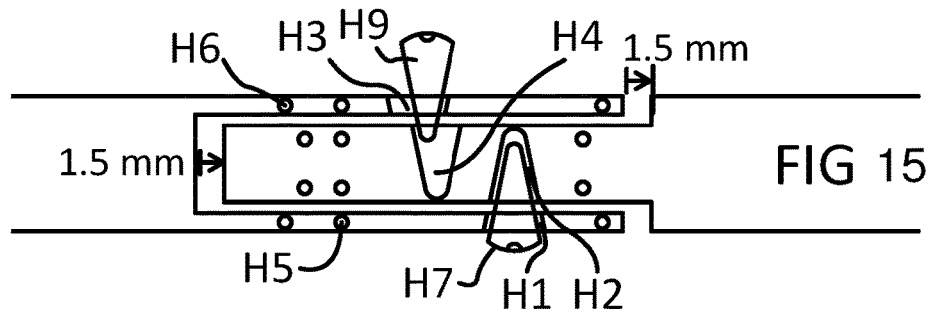
FIG 15
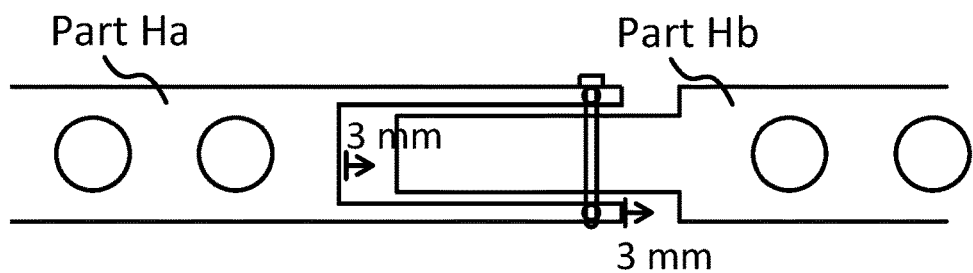
FIG 16
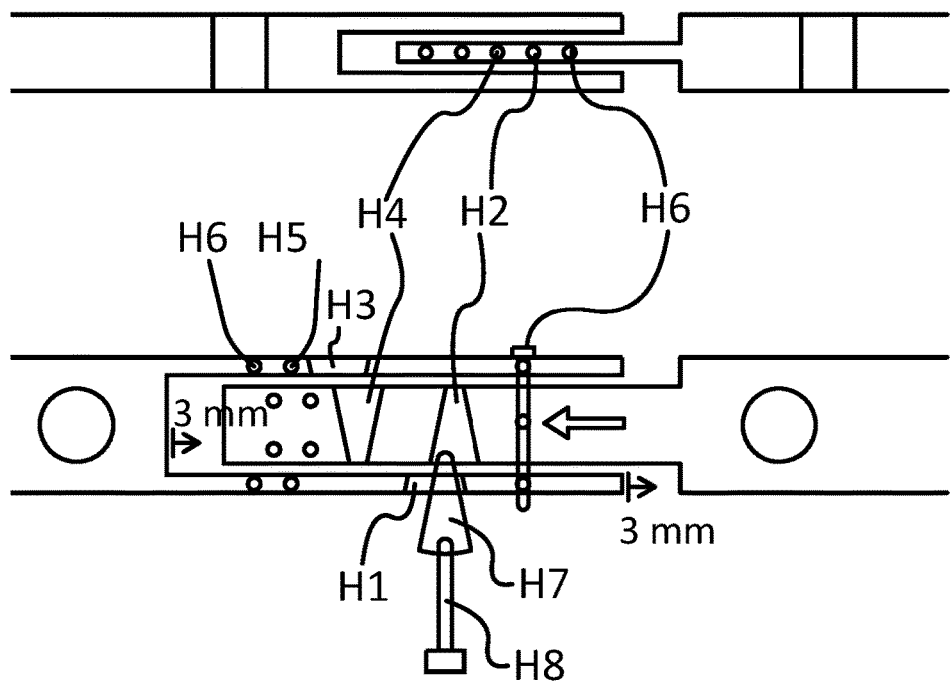

MODULAR BONE PLATE

PRIORITY BENEFIT

The present invention hereby claims the benefit of the prior provisional patent applications 61/978,841 and 61/984,748 filed on Apr. 12, 2014 and Apr. 26, 2014 respectively whose disclosures are incorporated by reference in their entirety.

BACKGROUND OF THE INVENTION

The human skeleton is composed of about 206 individual bones that perform a variety of functions, including support, movement, protection, storage of minerals, and formation of blood cells. A fractured or cut bone may be treated using a fixation device, which may reinforce the bone and may keep it aligned during healing. Fixation devices may include external fixation devices (such as casts and/or fixators) and/or internal fixation devices (such as bone plates, rods, and/or bone screws), among others.

Bone plates are sturdy internal devices, usually made of metal, that mount directly to the bone adjacent a fracture (or other bone discontinuity). To use a bone plate to repair a bone discontinuity, a surgeon typically (1) selects an appropriate bone plate, (2) reduces the discontinuity (e.g., sets the fracture), and (3) fastens the bone plate to bone fragments disposed on opposite sides of the discontinuity using suitable fasteners, such as screws and/or Wires, so that the bone plate spans the discontinuity and the bone fragments are fixed in position.

Standard bone plates and their associated fasteners may be insufficient to fix some orthopedic injuries in which bones are broken into several pieces. There are multiple kind of plate available for use but they are not multifunctional and do not offer flexibility in use when a different course of action is decided by the surgeon during the operation. For example, in treating articular comminuted fracture, usage of the plates is not easy because a variety of plate are available for different part of the body and they must be used for specific bones. The variety adds to the complexity of the operation.

SUMMARY OF THE INVENTION

The present teachings provide a system, including methods, apparatus, and kits, for fixation of different kinds of bone fracture where the same universal plate system is used for treating the fracture in any bones in the body. The modular plate system can be used for all part of the body and helps avoid problems during and after the surgery.

Almost all bone fixation plates have holes all along to be used for fixing to the bone using screws. The strength of plate decreases in the areas around the hole making the plate susceptible to breakage. A big problem in this practice is that the reduced mechanical strength leads to breakage. To overcome this problem a solid part without hole is positioned between two parts of the plate which are bound to the fractured bone with screws. This solid part connector has a higher strength hence more resistant to breakage.

In one embodiment the present invention provides systems, including new fixation methods and frames, apparatuses, and kits, for expanded fixation with modular bone plates. The modular bone plates may be constructed using a lot of different parts enabling enlargement of the bone plates' footprints on bones or to reshape the new frame for more stable fixation. This also allows for a variable type of bone plate fixation with screws and pins in different diameter and sizes.

A modular bone plate assembly may be pre-formed integrally with the bone plate and optionally assembled only during the surgery. This capability increases the stability of the fixation with while minimizing divesting bone and soft tissue detaching and facilitating the reduction of the bone fracture with bone holder by reducing interference. The method creates a variety of possibilities to form new frames for articular comminuted fracture, construct proper frames for osteoporotic fractures to prevent refracture, and enables easy shift from internal to external fixation in case an infection has been detected. Other applications include making external fixators similarly shaped as to the organ and near the skin for improving patient's experience, fixation of small fractured parts that are not accessible from the main plate and are far from the pathway of the main plate, easy pin-plate fixation and connecting the pin in a wide range of direction angles with respect to the plate, compressing the fracture site for better union, if non-union occurred, without need to change the plate and the location of plate, setting the length of plate with special movable parts or attach another modular part without need to replace or remove the main plate. Overall this system is multi-optional fixation device that assembles according to the needs during the surgery that mitigates the complication of operation with minimal interference.

The fixation device may span one or more discontinuities in the bone. For example, the fixation device may span a transverse fracture (or other transverse discontinuity) and an additional fracture (or other additional discontinuity), e.g. a fracture that extends obliquely and/or axially in the bone. The fixation device may include some part of a modular plate different in shape and function that corresponding to needs during the surgery, assembles together and forms a new frame that works best for each fracture.

The modular plate may have any suitable relative orientations. In some examples, the bone plate may extend generally along the bone, to span the transverse discontinuity and stabilize it. The system can extend partially around the bone, to span the additional discontinuity and stabilize the bone with respect to the additional discontinuity and thus expand the fixation capability of the bone plate.

In one embodiment, the present invention introduces a system for perfecting bone contact in bone fixation by compressing the bone parts against each other and moving them a total bone displacement distance, comprising: a rail comprising a fork with elongated handle, the handle having a first plurality of holes on for fastening to a first part of a fractured bone, the fork comprising two parallel plates connected to the handle, positioned a first distance apart, a second plate with a proximal and a distal end and with a second plurality of holes on a distal end for fastening to a second part of the fractured bone on the distal end Wherein the parallel plates of the fork extend outward from the fractured edge of the first part of the fractured bone a first extended region, and the second plate, affixed on the distal end of the second plate to the second part of the fractured bone such that the proximal end of the second plate extends outward from the fracture edge of the second part of the fractured bone a second extended region; a first plurality of conically-shaped holes made into each of the parallel plates of the fork, identically and perfectly aligned, such that the holes being spaced a first pitch apart, a second plurality of conically-shaped holes made into the second plate, spaced a second pitch apart; wherein the first pitch is different from the second pitch and that the width of the second plate, the width as related to insertion of second plate between the two parallel plates of the fork, is less than the first distance; wherein the second plate is slidably positioned between the two parallel plates of the fork such that the first extended region and second extended regions at least partially overlap, to approach the first part and the second part of the fractured bone to each other; wherein the overlapping is performed by creating a desired alignment position, comprising aligning the fork with the second plate such that at least one of the holes on the first plurality of conically-shaped holes, that is the first target hole, is offset with at least one of the holes on the second plurality of conically-shaped holes that is the second target hole, and the amount of offset is equal to or a fraction of the total bone displacement needed, and a first conically shaped wedge of a plurality of conically shaped wedges is passed through the first target hole and pushed toward insertion into the second target hole such that the offset is eliminated by pushing the second bone part toward the first bone part.

After eliminating the first offset, the process is similarly repeated by inserting another conically shaped wedge into another one of conically shaped holes to eliminate a second offset.

In one embodiment of the present invention, the fork and the second plate are further fastened to pieces in customizable main plates at their distal ends, wherein the pieces are fastened to the first and second bone parts, respectively and the fork and the second plate are not directly fastened to their corresponding bone parts. Further, when fastened, the fork and the second plate create angles between 0 and 90 degrees with corresponding pieces in customizable main plate systems.

In one embodiment of the present invention, each of distal end of the fork and the distal end of the second plate comprise at least three adjustment holes for fixing the angles to stay between 0 and 90 degrees by inserting pins or screws in the adjustment holes.

The fork and the second plate form a rail-plate structure and two of the pieces of two customizable main plate systems are connected to the two ends of the rail-plate thereby one connecting to the distal end of the fork and the other connecting to the distal end of the second plate, wherein at least one of the two pieces of the customizable main plates includes two opposite recesses made in its mid-section.

A bone clamp is further used to hold a bone-main plate assembly and the arms of the bone clamp are placed at the recesses to thereby hold the bone-main plate assembly. Further, the bone clamp has curved arms to allow for extra space for more easily placing the customizable main plate assembly system on the bone parts while being held by the bone clamp.

A method for perfecting bone contact in bone fixation by compressing the bone parts against each other and moving them a total bone displacement distance, comprising the steps of providing a rail comprising a fork with elongated handle, the fork comprising two parallel plates with a first distance apart, affixing the elongated handle of the fork having a first plurality of holes on the distal end to a first part of a fractured bone, affixing a second plate with a proximal end and a distal end and with a second plurality of holes on the distal end to a second part of the fractured bone on the distal end wherein when the elongated handle is affixed to the first part of the fractured bone, the parallel plates of the fork extend outward from the fractured edge of the first part of the fractured bone a first extended region, and the second plate is affixed on the distal end to the second part of the fractured bone such that the proximal end of the second plate extends outward from the fractured edge of the second bone a second extended region, a first plurality of conically-shaped holes made into the first extended region on each of the parallel plates of the fork identically, such that the holes being spaced a first pitch apart, a second plurality of conically-shaped holes made into the second extended region on the second plate, spaced a second pitch apart wherein the first pitch is different from the second pitch, and further the width of the second plate, the width as related to insertion of second plate between the two parallel plates of the fork, is less than the first distance, and the second plate is slidably positioned between the two parallel plates of the fork such that the first extended region and second extended regions at least partially overlap, to approach the first part and the second part of the fractured bone toward each other, and wherein the overlapping is performed by aligning the fork with the second plate such that at least one of the holes on the first plurality of conically-shaped holes, the first target hole, is offset with at least one of the holes on the second plurality of conically-shaped holes, the second target hole, and the amount of offset is equal to or a fraction of the total bone displacement needed, creating a desired alignment position, wherein a first conically shaped wedge of a plurality of conically shaped wedges is passed through the first target hole and pushed toward insertion into the second target hole such that the offset is eliminated by pushing the second bone part toward the first bone part.

In one embodiment, after eliminating the first offset, the process is similarly repeated by inserting another conically shaped wedge into another one of conically shaped holes to eliminate a second offset.

In one embodiment, a bone-main plate assembly is formed by placing the piece on a bone and then a bone clamp is used to hold the bone-main plate assembly wherein the arms of the bone clamp are placed at the recesses to thereby hold the bone-main plate assembly for bone fixation.

In one embodiment, the present invention comprises a method of bone fixation using a customizable main plate system assembled using an array of pieces and two bone clamps comprising the steps of holding two parts of a broken bone aligned to each other in a proper position by holding each part with a bone clamp; placing the customizable main plate system on the bone by sliding through the openings between the arms of the bone clamps; rotating the customizable main plate system around its longitudinal axis by a proper angle such that the bottom surface of the customizable main plate system lies over the surface of the bone parts while the bone clamps continue to hold, and using screws, fastening the customizable main plate system to the bone parts, thereby fixate them.

In one embodiment, customizable main plate system includes recesses on its mid-section to accommodate for the arms of the bone clamps thereby facilitating the step of rotating the customizable main plate assembly system around its longitudinal axis.

In one embodiment, at least one of the bone claims have curved arms to allow for an extra space for more easily rotating the customizable main plate assembly system.

BRIEF DESCRIPTION OF THE DRAWINGS

FIGS. 15, 16 and 17 show the usage of rail plate for compressing the fractured bone after attaching the plate to the bone in nonunion state. This way the fracture site is compressed without removal of plate.

DETAILED DESCRIPTION OF THE PREFERRED EMBODIMENTS

The following patents and patent applications are incorporated by reference in their entirety: US20040102777, US20040102776, U.S. Pat. No. 8,177,819, U.S. Pat. No. 8,231,662 B2, U.S. Pat. No. 7,235,079 B2, U.S. Pat. No. 7,635,365, US20040260291, U.S. Pat. No. 8,177,819 B2, US20050192578 A1, U.S. Pat. No. 8,177,819 B2, U.S. Pat. No. 7,537,596, US20050240187, and U.S. Pat. No. 7,785,355.

The following sections describe further aspects of the present teachings, including, among others, (I) modular bone plate and special different part with different capability, (II) methods of fixing bones using modular bone plate, (III) kits, and (IV) examples.

Disclosures of Patent Applications

The Modular Bone Plate

Figure 1:
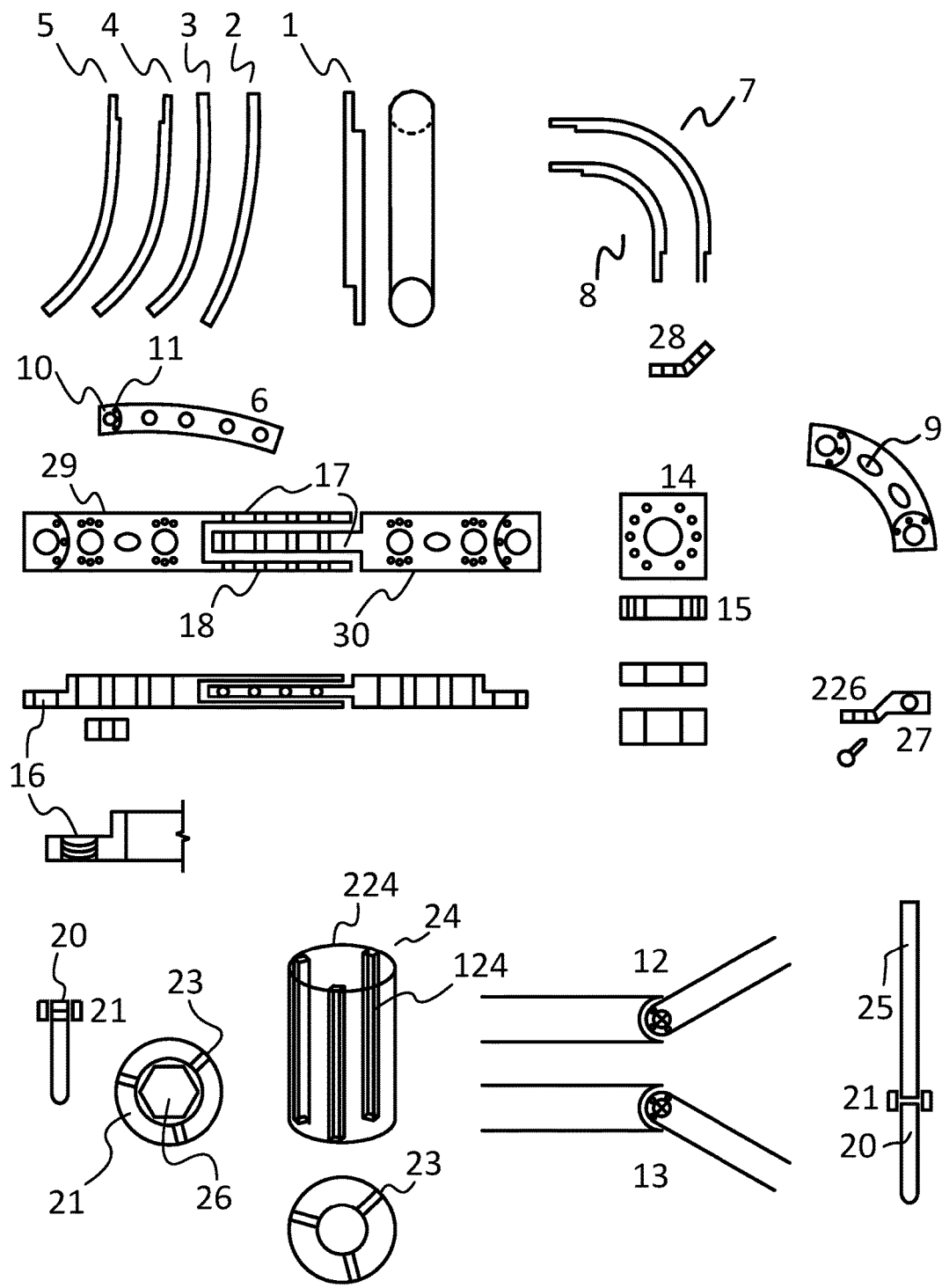
FIG. 1 shows the different part of modular plate setting including plate screw and wrench, spacer, rail plate, twisted plate, and different kind of curved wing plate that is used for fixation of a fractured bone.

Modular system plates are configured using an array of different plates with different sizes and shapes which can be assembled to achieve the suitable plate during the operation. FIG. 1 shows by numerals 1-8 the usable components for the multi-part tool including curved plate in different angles and sizes (Straight plate 1 can have different sizes not shown in FIG. 1).

The following descriptions refer to FIG. 1. The opening A9 on the plate can be threaded or non-threaded that is configured at the end of modular part plate for fixating to member A16. Two kinds of opening exist at the end of modular plate (MP). Central threaded opening A10 and three small holes A11 around it. Two plate at the end part fix to each other in the prepared space. Before fastening the screw in the central hole, the extension member can rotate around another plate and small hole around the central hole determine the amount of rotation and when small hole of two plate are aligned with each other, the screw is fastened and then a pin trap in inserted in the small hole as an accessory fixator as shown in FIGS. A12 and A13.

The number of small holes determines the smallest rotation angle can be achieved. If a higher rotation angle is needed, a spacer A14 with more small holes can be affixed to the end of the plate to fix the two plates in the angle needed and then the pin in inserted in the new hole that permits the amount of desired rotation.

A rail plate consists of two parts A29, A30 with sliding sections A17 slide against each other to be fixed them in length needed. The fixation is performed using screw inserted into the special opening A18.

Special screw in one embodiment of this invention consists of two parts: head A21 and body A20. The body screw can be inserted into the heads A21 of different sizes. It is possible to separate the head A21 from the body A20 without withdrawing the body from the bone. For this purpose, the special wrench A24 is used. Wrench 24 has teeth A124 inside a tube A224 that matches with the groove A23 over the head of screw A21. The wrench A24 grips on the head screw and without turning the body A20 unscrews the head A21 from the body A20. After the head A21 is separated from the body A20, the plate A29-A30 can be removed from the bone to, for instance, connect an extension A25, to the main body which has remained in the bone. This system for example can be used to shift from an internal fixation to an external fixation.

Twisted modular plate (MP) permits fixation of the part of bone not in the pathway of the plates A226, A27, A28, with different angles and sizes.

Curved wing plates A7 and A8 are used for wrapping around the bone as much as possible if needed.

Figure 2:
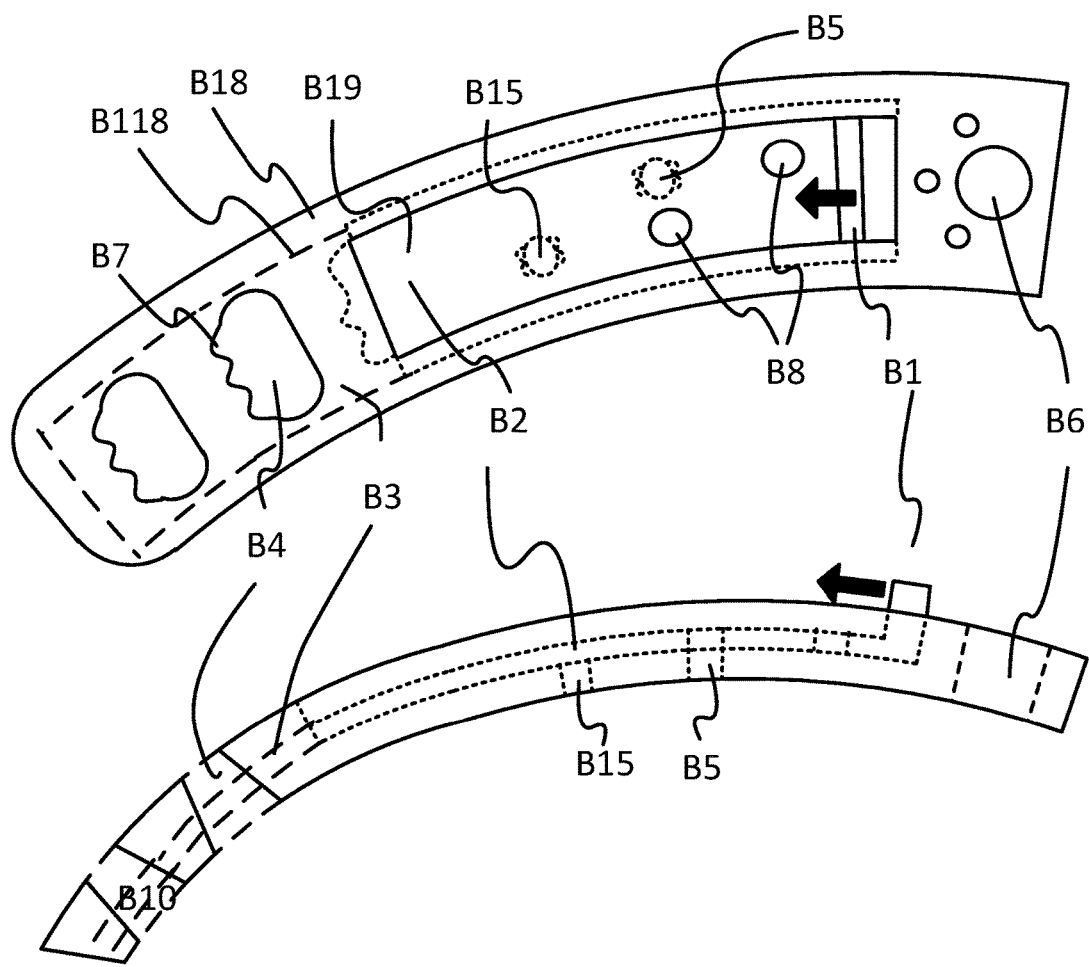
FIG. 2 shows a special part of the system named pin-plate connector, a special curved wing plate use for fixation of pin in each direction to the plate, and the holes on the plate made for pin fixation.
Figure 3:
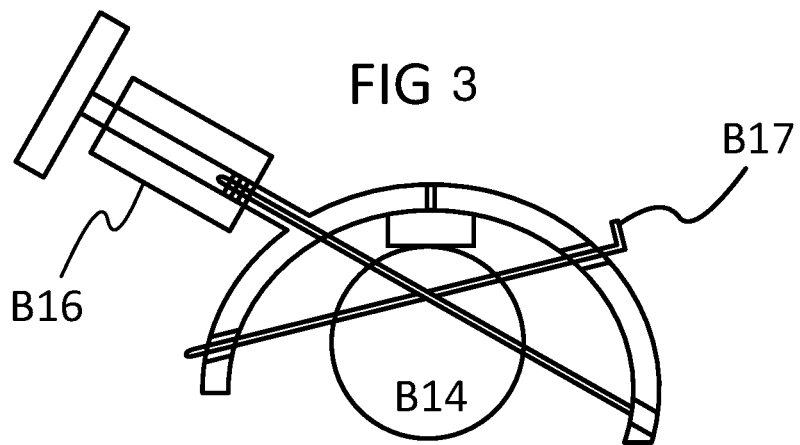
FIG. 3 shows the plate over the bone and position of the pin and plate relative to the bone and the efficacy of pin-plate curved wing connector.
Figure 4:
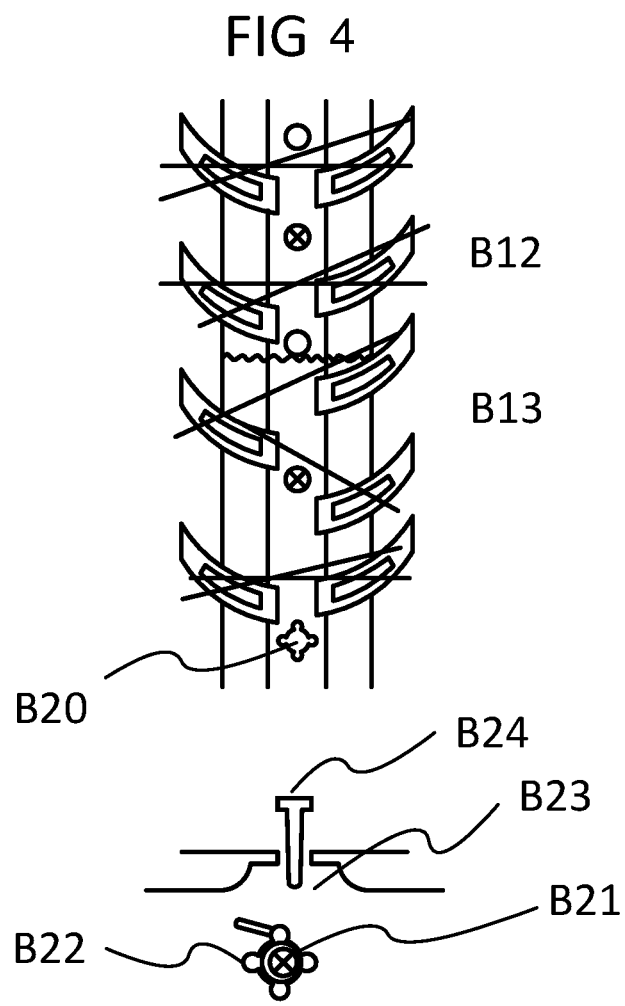
FIG. 4 shows the special fixation method used for osteoporotic bones with use of pin-plate curved wing connector instead of screw plate fixation.

The following descriptions refer to FIGS. 2-4.

Pin-plate Curved Wing Plate (CWP) is specialized for fixing the pin to the plate in different directions and consists of two parts: base part B18, and movable part B19. Base part is a CWP part with hole specialized for pin fixation, and movable part, that moves and traps the pin in hole B4, and fix it.

Bone plates as described herein generally comprise any relatively low-profile (or plate like) fixation devices configured to stabilize at least one bone by attachment to the bone. The fixation device may be configured to span any suitable bone discontinuity (or discontinuities) and for each part of bone a suitable figured plate existed so that the fixation device fixes the relative positions of bone fragments (and/or bones) disposed on opposing sides of the bone discontinuity (or discontinuities). Alternatively, or in addition, the fixation device may reinforce a bone lacking a discontinuity.

Suitable discontinuities may occur naturally and/or may result from injury, disease, and/or surgical intervention, among others. Accordingly, exemplary discontinuities for use with the fixation devices described herein may include joints, fractures (breaks in bones), osteotomies (cuts in bones), and/or nonunions (for example, produced by injury, disease, or a birth defect), among others. all of them can managed with modular bone plate.

The bone plates described herein may be configured for use on any suitable bone, in any suitable animal species, including human, equine, canine, and feline species, among others. Exemplary bones may include bones of the arms (radius, ulna, humerus), legs (femur, tibia, fibula, patella), hands/Wrists (e.g., phalanges, metacarpals, and carpals), feet/ankles (e.g., phalanges, metatarsals, and tarsals), vertebrae, scapulas, pelvic bones, cranial bones, ribs, and/or clavicles, among others. Particular exemplary regions of bones Where the bone plates described herein may be secured include a proximal portion and/or a lateral surface of the femur, tibia, humerous, radius bone.

Particular fractures where the bone plates described herein may be suitable include bones with multiple fractures creating a plurality of bone fragments. One or more of the fragments may not be suitably disposed for securing directly and/or sufficiently to a bone plate with a fastener placed through an opening of the bone plate and into the fragment because of, for example, the size, position, structure, etc., of the one or more fragments.

Each part of modular bone plate may be configured to be disposed in any suitable position relative to its target bone. The bone plate (or a plate portion) may be configured to be disposed in contact with an exterior surface of the bone and thus maybe positioned at least substantially (or completely) exterior to the bone. Alternatively, the bone plate may be configured to be disposed at least partially interior to a bone, that is, opposed to (normally) interior bone surfaces when secured to the bone. The interior surfaces of the bone may be accessed during installation of the bone plate (such as by punching the bone plate through the exterior bone surface) and/or may be accessible due to a break, a cut, and/or the like.

The bone plates may be formed of any suitable material(s). The bone plates may be of a sturdy yet malleable construction. Generally, the bone plates should be stiffer and stronger than the section of bone spanned by the plates, yet flexible (e.g., springy) enough not to strain the bone significantly. A bone plate of the present teachings may be at least substantially formed of, or may include, any suitable biocompatible material(s) and/or bioresorbable material(s). Exemplary biocompatible materials that may be suitable for the bone plate include (1) metals/metal alloys (for example, titanium or titanium alloys, alloys With cobalt and chromium (such as cobalt-chrome), stainless steel, etc.); (2) plastics (for example, ultra-high molecular Weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) ceramics (for example, alumina, beryllia, calcium phosphate, and/or Zirconia, among others); (4) composites (for example, carbon-fiber composites); (5) bioresorbable (bio absorbable) materials or polymers (for example, polymers of ot-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-[3-hydroxybutyrate, poly-[3-hydroxypropionate,poly[3-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.); and/or the like. In some examples, one or more of these materials may form the body of a bone plate and/or a coating thereon.

The bone plates may be configured to reduce irritation to the bone and surrounding tissue. For example, the bone plates may be formed of a biocompatible material, as described above. In addition, the bone plates may have a low and/or feathered profile to reduce their protrusion into adjacent tissue and rounded, burr-free surfaces to reduce the effects of such protrusion.

The bone plates described herein may be sized and shaped to conform to particular portions of a bone (or bones). The plates may be generally elongate, With a length L, a Width W, and a thickness T. Here, length L>Width W>thickness T. In use, the long axis of the bone plates (or of a plate portion) may be aligned With the long axis of the corresponding bone, and/or may extend obliquely and/or transversely relative to the bone's long axis. The length and/or Width of the bone plates may be varied according to the intended use, for example, to match the plates with a preselected region of bone(s) and/or a particular injury to the bone. For example, the plates may be generally linear for use on the shaft of a long bone and/or may have a nonlinear shape, such as for use near an end of a bone and/or for transverse placement on the shaft, among others. In some examples, the modular bone plates maybe configured to wrap at least partially around a bone, so that portions of each plate are disposed on distinct sides and/or generally opposing sides/surfaces of a bone. In some embodiments, the bone plates may be configured for use on both sides of the body/skeleton, such as when the bone plates are bilaterally symmetrical. In some embodiments, the bone plates may be asymmetrical and configured for use on either the left or the right side of the body/skeleton, but not both. The bone plates may include inner (bone-facing) and outer (bone-opposing) surfaces. One or both of these surfaces may be contoured generally to follow an exterior surface of a target bone (or bones) for Which a bone plate is intended, so that the bone plate maintains a low profile and fits onto the bone(s). For example, the inner surface of a plate may be generally complementary in contour to the bone surface. The outer surface of the plate also may correspond in contour to the bone surface and may be generally complementary to the inner surface of the plate. The bone plates may be partially and/or completely pre-contoured, at the time of manufacture, allowing practitioners to apply them to bone(s) with little or no additional bending at the time of application.

Alternatively, or in addition, the bone plates may be custom-contoured by practitioners before and/or during installation onto bone. The thickness of the bone plates may be defined by the distance between the inner and outer surfaces of the plates. The thickness of the plates may vary between plates and/or within the plates, according to the intended use. For example, thinner plates may be configured for use on smaller bones and/or on bones or bone regions where soft tissue irritation is a greater concern. Thickness may be varied within the plates. For example, the plates may become thinner as they extend over protrusions (such as processes, condyles, tuberosities, and/or the like), reducing their profile and/or rigidity, among others. Alternatively, or in addition, the thickness may vary as an interior portion of the bone plate extends into bone, for example, becoming thinner to facilitate insertion of this interior portion or thicker to increase structural stability. The thickness of the plates also may be varied to facilitate use, for example, to make the plates thinner where they typically need to be deformed by bending and/or twisting the plates, such as at a junction (or bridge region) between plate portions. In this way, the plates may be thicker and thus stronger in regions where they may not need to be contoured, such as along the shaft of the bone.

The bone plates generally include a plurality of openings. The openings may be adapted to receive fasteners for securing the plates to bone. Alternatively, or in addition, one or more of the openings may be configured to alter the local rigidity of the plates, to permit the plates to be manipulated with a tool (such as an attachable handle), to facilitate blood flow to bone regions where the bone plates are installed, to promote healing, and/or the like.

In some examples, one or more of the openings may be adapted to receive a fastener that attaches the plate to a corresponding extension member and/or to receive a projection of the extension member. These openings may extend through the bone plates (between inner and outer surfaces) and/or may extend at least substantially parallel to the inner and/or outer surfaces of the bone plates.

The openings may have any suitable positions, sizes, and/or densities within each portion of a bone plate. The openings may be arrayed generally in a line along a portion of the plate, for example, centered across the width of the plate. Alternatively, the openings may be arranged nonlinearly, for example, disposed in an arcuate, staggered, or other two-dimensional (or three-dimensional) arrangement.

The openings may have any suitable shape and structure. Exemplary shapes may include circular, elongate (such as elliptical, rectangular, oval), etc. The openings may include counter bores. The counter bores may be configured, for example, to receive a head of a bone screw, to reduce or eliminate protrusion of the head above the outer surface of the plate. The openings may be threaded or non-threaded, and each bone plate may include one or more threaded and/or non-threaded openings. In some embodiments, the plates may include one or a plurality of elongate openings (for example, oval openings) extending axially, obliquely, and/or transversely within each bone plate. The elongate openings may be compression slots that include contoured counter bores to provide compression when heads of bone screws are advanced against the counter bores. Alternatively, or in addition, the elongate openings may be used to adjust the position of bone plates and/or plate portions relative to bone before the plates are fully secured to the bone.

In some examples, the bone plates may include one or more projections. The projections may extend, for example generally orthogonal from the inner surface of the bone plates toward bone. Alternatively, or in addition, the projections may extend generally outward from the outer surface of the bone plates. In either configuration, the projections may be configured to engage corresponding openings of extension members. The projections may be sharp or blunt according to their intended use. For examples, sharp projections may be configured as prongs that penetrate bone to restrict movement of the bone plates. Prongs may be used in place of, or in addition to, bone fasteners, for one or more portions of each bone plate. Blunt (or sharp) projections, such as ridges or knobs (or tines), may be configured formatting with openings/depressions of extension members or as spacing members that elevate the bone plates from the bone surface.

The bone plates may have at least one, and generally two or more, plate portions (or anchor portions) configured to be secured to different regions of a bone (or bones). Each plate portion may be structured for a specific region of a bone. For example, the bone plates may include a proximal plate portion for attachment to a more proximal region of a bone, and a distal plate portion for attachment to a more distal region of the same bone. Alternatively, or in addition, the bone plates may include an exterior plate portion configured to fit against an exterior surface region of bone adjacent a bone discontinuity, and/or an interior plate portion configured to be received in an interior (e.g., recessed, resected, and/or excavated) region of bone adjacent the bone discontinuity.

The plate portions of a bone plate may have any suitable connection. In some examples, the plate portions may be formed integrally, so that one piece of the bone plate includes the plate portions. Alternatively, plate portions may be formed as separate pieces. The separate pieces may be connected by any suitable connection and/or joint, including a fastener(s), welding, a hinge joint, a ball-in-socket joint, and/or the like. Further aspects of bone plates having adjustable joints are described in the following patent application, which is incorporated herein.

The plate portions of a bone plate may have any suitable relative disposition. The plate portions may be disposed such that they are substantially collinear and/or parallel, oblique, or substantially transverse to one another.

The relative disposition may be fixed and/or adjustable. In some examples, the plate portions may be connected integrally by a deformable bridge region, so that the bone plate can be bent pre- and/or peri-operatively to adjust the relative disposition of the plate portions. Alternatively, the plate portions may be distinct pieces connected, for example, through an adjustable joint, as described above.

Each plate portion may have one or more openings and/or other receiving structures. Each opening may be configured to receive a fastener for placement of the bone fastener into bone and/or for connection of the plate portion.

Method of Fixing Bones Using Modular Bone Plate

The system of the present teachings may include methods of fixing bones by installing bone plates and corresponding extension members on the bones. The methods may include any suitable combination of the following steps, performed in any suitable order and any suitable number of times.

A bone for fixation may be selected. Any suitable bone may be selected having one, two, or more discontinuities, such as a femur bone fractured at two or more positions to create three or more bone fragments. A bone plate may be selected for fixation of the bone. The bone plate may have any suitable combination of the features described elsewhere in the present teachings. The practitioner selects one of different model of plate suitable for the bone that is available as presented herein. For example, a straight plate A1 can be chosen as a base.

Each bone plate may need to be configured to be disposed in any suitable position relative to its target bone. The bone plate (or a plate portion) may be configured to be disposed, in contact with an exterior surface of the bone and thus may be positioned at least substantially (or completely) exterior to the bone. But when using the modular system, appropriate parts can be attached to provide a more perfect contact with bone and improve the positioning of the assembled plate over the bone.

Figure 5:
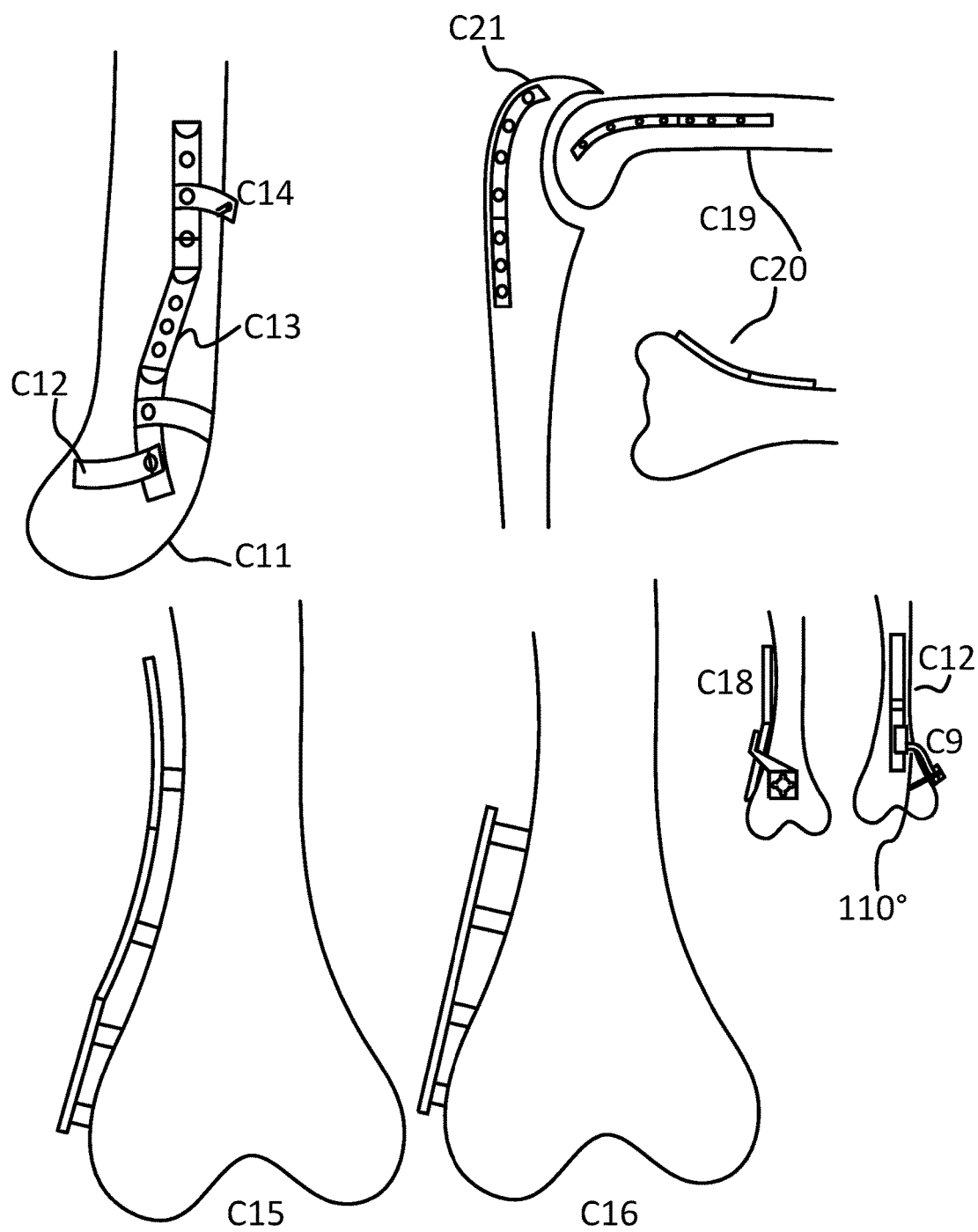
FIG. 5 shows using the modular plate system and the use of twisted plates for different parts of body and bone (C18). For example in the situations where tibia tuberosity has been fractured, the twisted plate can be used. One end of the twisted plate is affixed to the main plate that is fixed to the bone and the other end is twisted such that it can be placed and properly conform to the surface at the place of the tibial tuberosity. Similarly such a system with twisted plates can be used to treat anterior wall of distal tibia and distal radius fracture and in any situation where a straight or curved plate is incapable of reaching to a bone fragment.

As shown in FIG. 5, appropriate parts are attached to cross the curve on each bone C1 proximal tibia C3 distal tibia C11 distal femur C17 and distal radius, distal humorous C19, C20 and olecranon C21. Also plate can be positioned in optimal direction and attach the part in optimal angle that permit the plate lie over the bone in the best situation C12, C13.

Figure 6:
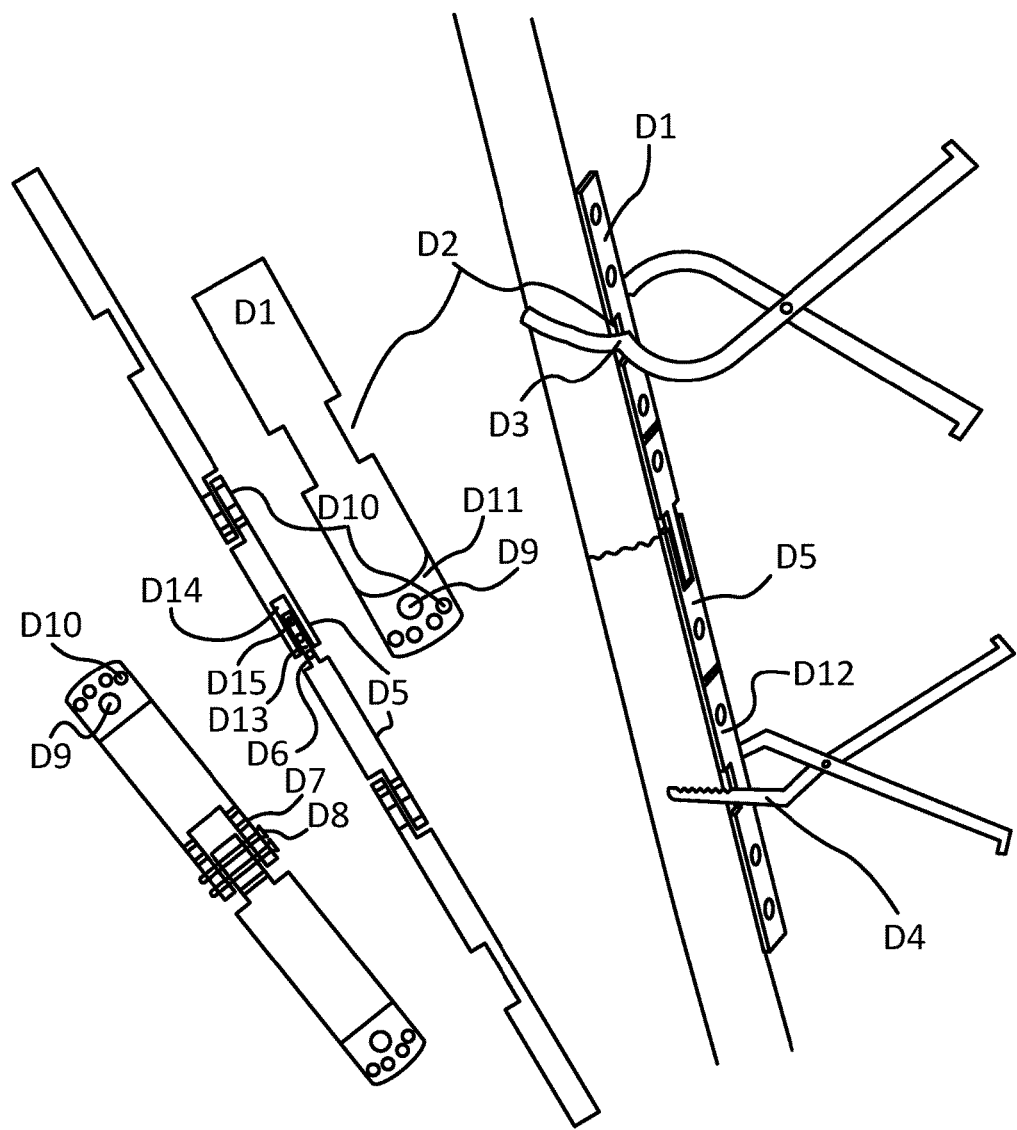
FIG. 6 shows the method for using the modular plate system for fixation of the bone and usage of the rail plate to adjust the length of plate as needed during the surgery and the use of special parts made for reduction of bone without interference with bone holder.

As shown in FIG. 6, first the fractured bone is reduced with bone clamp and maintained then special part D1 that has a section D2 with reduced width in the middle is positioned over the bone. Because of the narrow width, no interference exists between the plate and the edge of the blade of bone holder D3 or between the plate and the edge of handle of bone holder D4. Therefore, the plate lies over the bone in full contact without any interference. This is done similarly at the other side of the fracture by putting another plate D12 of this type followed by positioning a rail plate D5 between them and connecting them. The curved edge of the special part D11, allows the practitioner to rotate the rail plate, change the angle and position the rail plate in a proper direction aligned with the bone.

After the desired angle has been obtained, it is fixed using the hole D9 and connect the part D1 and rail plate D5. To lock the angle, one of holes D10 of rail plate is used. To reach a desired length or to reach part D12 on the opposite side, plate D5 with various lengths can be used (as shown in FIG. 1) or several number of plates D5 can be used to create a bone plate with a desired length. Alternatively or in addition, the rail D13 can be adjusted to create a desired length. The rail D13 is a tongue-shaped blade that is placed and moved in the provided space D13 of part 5. After selecting the suitable length, a selected hole D7 is aligned with a selected hole D15 and the plate is fixed using a screw. Alternatively or in addition, before putting the screw in the hole D10 all three parts are bent relative to each other to in the hole or hinge D9 on both sides of rail plate to reach the best alignment. The modular bone plate may be secured to the bone, before, during, and/or after reduction. (Bone plates secured before or during reduction typically would be secured only partially until the reduction is completed.) Securing the bone plate may be performed by placing one or more fasteners, such as screws, wires, pins, etc., through openings of the bone plate and into the fractured bone. Generally, the bone plate may be secured to opposing sides of a discontinuity, such as a fracture, in the bone.

An extension member may be selected for additional fixation of the bone. The extension member may be selected from a set of extension members differing in overall size, shape, length, width, handedness, connection site on the bone plate, etc. The extension member may be further contoured pre- and/or post-operatively (such as by bending the extension member), for example, to adjust how the extension member fits onto the bone plate, bone, and/or over soft tissue, or the extension member may be used without further contouring. In examples where the extension member is formed integrally with the bone plate, and/or supplied in a connected configuration, selection of the bone plate may also select the extension member.

The extension member may be coupling to the bone plate. This step of coupling may be performed before, during, and/or after the bone plate is secured to the bone. Coupling may connect the extension member to the bone plate in an adjustable configuration (e.g., movable pivotably and/or translationally with respect to the bone plate) and/or in a fixed configuration. Coupling may include opposing the extension member to a surface of the bone plate, such as the inner or outer surface of the bone plate. This apposition may align connective features of the bone plate and the extension member. Accordingly, this apposition also may include placing a projection(s) of the extension member into an opening(s) of the bone plate, and/or a projection(s) of the bone plate into an opening(s) of the extension member. The projections may be configured to restrict pivotal and/or translational motion of the extension member relative to the bone plate. The projections thus may fit snugly into the openings.

The step of coupling the extension member to the bone plate may include placing a fastener(s) through an opening(s) of the bone plate and/or extension member. In some examples, the fastener may have an external thread that engages an internal thread of an opening of the bone plate and/or of the extension member. Alternatively, or in addition, the fastener may be received in underlying bone, such as when the fastener extends through aligned openings of the bone plate and the extension member and threads into bone. The head of the fastener may engage the bone plate and/or the extension member, based, for example, on the relative disposition of these components and the direction in which the fastener is placed through the openings.

The extension member may be connected to bone at a surface position of the bone that is spaced from the bone plate. Connection of the extension member at this spaced position may include placing prongs or other projections of the extension member into bone. Alternatively, or in addition, the connection of the extension member to bone may include securing a spaced portion of the extension member to bone by placement of a fastener(s) through an opening(s) of the extension member and into the bone. The steps described above may be used to fix multiply fractured bones. For example, the bone plate may fix a bone relative to a first fracture of a bone, and the extension member may fix the bone relative to a second fracture of the bone.

Kits

The system of the present teachings may provide kits for fixing bones. The kits may include some part of modular bone plates, that assemble together to achieve a suitable frame and best position for the bone plate contact, fasteners (such as bone screws, wires, or the like) for securing the bone plate(s) and/or extension member(s) to bone and/or each other, a measurement device, a guide device, a positioning jig, a drill(s), one or more clamps, instructions for use, and/or the like. Some or all of the components of each kit may be provided in a sterile condition, such as packaged in a sterile container, and/or may be sterilizable (e.g., autoclavable).

In one embodiment, the present invention is a system for bone fixation comprising a pin-plate curved wing plate (pin-plate CWP) including a superior movable part and at least one special hole for securing a pin, at least one modular main plate comprising a plurality of smaller plates with different sizes and round ends, wherein the plurality of smaller plates are rotatably connected to form the modular main plate, a plurality of cylindrical spacers wherein each of the plurality of curved wing plates comprising at least one bone plate engagement portion, at least one bone fixation portion and at least one intercalating portion, wherein the intercalating portion is positioned between the at least one bone plate engagement portion and the at least one bone fixation portion; wherein an array of holes are provided on each of the plurality of curved wing plates and the number of the holes in the array of holes is related to a size of the curved wing plate.

In one embodiment, the present invention is a system for perfecting bone contact in bone fixation by compressing the bone parts against each other and moving them a total bone displacement distance, comprising a rail comprising a fork with elongates handle, the handle of the fork having a first plurality of holes on the distal end for fastening to a first part of a fractured bone, the fork comprising two parallel plates with a first distance apart, a second plate with a proximal and a distal end and with a second plurality of holes on a distal end for fastening to a second part of the fractured bone on the distal end wherein the parallel plates of the fork, affixed to the first part of the fractured bone, extend outward from the fractured edge of the first part of the fractured bone a first extended region, and the second plate, affixed on the distal end of the second plate to the second part of the fractured bone such that the proximal end of the second plate extends outward a second extended region, a first plurality of conically-shaped holes made into the first extended region on each of the parallel plates of the fork in identically and perfectly aligned, and such that the holes being spaced a first pitch apart, a second plurality of conically-shaped holes made into the second extended region on the second plate, spaced a second pitch apart such that the first pitch is different from the second pitch wherein the width of the second plate, the width as related to insertion of second plate between the two parallel plates of the fork, is less than the first distance wherein the second plate is slidably positioned between the two parallel plates of the fork such that the first extended region and second extended regions at least partially overlap, to connect the first part and the second part of the fractured bone wherein the overlapping is performed by creating a desired alignment position, comprising aligning the fork with the second plate such that at least one of the holes on the first plurality of conically-shaped holes, that is the first target hole, is offset with at least one of the holes on the second plurality of conically-shaped holes that is the second target hole, and the amount of offset is equal to or a fraction of the total bone displacement needed, wherein a first conically shaped wedge of a plurality of conically shaped wedges is passed through the first target hole and pushed toward insertion into the second target hole such that the offset is eliminated by pushing the second bone part toward the first bone part.

In one embodiment the present invention is a method for perfecting bone contact in bone fixation by compressing the bone parts against each other and moving them a total bone displacement distance, comprising the steps of providing a rail comprising a fork with elongates handle, the fork comprising two parallel plates with a first distance apart, affixing the elongated handle of the fork having a first plurality of holes on the distal end to a first part of a fractured bone, affixing a second plate with a proximal end and a distal end and with a second plurality of holes on the distal end to a second part of the fractured bone on the distal end wherein when the elongated handle is affixed to the first part of the fractured bone, the parallel plates of the fork extend outward from the fractured edge of the first part of the fractured bone a first extended region, and the second plate is affixed on the distal end to the second part of the fractured bone such that the proximal end of the second plate extends outward a second extended region, a first plurality of conically-shaped holes made into the first extended region on each of the parallel plates of the fork identically, such that the holes being spaced a first pitch apart, a second plurality of conically-shaped holes made into the second extended region on the second plate, spaced a second pitch apart such that the first pitch is different from the second pitch wherein the width of the second plate, the width as related to insertion of second plate between the two parallel plates of the fork, is less than the first distance and the second plate is slidably positioned between the two parallel plates of the fork such that the first extended region and second extended regions at least partially overlap, to connect the first part and the second part of the fractured bone wherein the overlapping is performed by aligning the fork with the second plate such that at least one of the holes on the first plurality of conically-shaped holes, the first target hole, is offset with at least one of the holes on the second plurality of conically-shaped holes, the second target hole, and the amount of offset is equal to or a fraction of the total bone displacement needed, creating a desired alignment position, wherein a first conically shaped wedge of a plurality of conically shaped wedges is passed through the first target hole and pushed toward insertion into the second target hole such that the offset is eliminated by pushing the second bone part toward the first bone part.

In one embodiment, after eliminating the first offset, the process is similarly repeated by inserting another conically shaped wedge into another one of conically shaped holes to eliminate a second offset.

In one embodiment, the present invention is a system used for external fixation of bones in a bone reduction operation, comprising a clamp comprising a first plate which is hollow with a window having a first cavity, the cavity having a height, a width and a length, the first plate having a plurality of holes on a proximal and a distal section, a second plate with a second thickness, a second width and a second length wherein the second thickness, the second width and the second length are less than the height, the width and the length, respectively wherein the plurality of holes on proximal section allows the passage of pins, wherein the second plate is entirely positioned inside the first cavity, slidably movable towards the proximal section using a handle that protrudes out from the window in the walls of the first cavity, and wherein after the pin is passed through the hole on the proximal section, the second plate is pushed to depress the pin and thereby stop the movement of the pin, the system further comprises providing an array of holes on the first and second plates for fixing the position of the second plate relative to the first plate after proper positioning.

In one embodiment of the present invention, one of the plurality of holes on the proximal section are large enough to allow angled passage of pins, the pins pass with an angle defined as angle constructed between the body of the pins and the first plate and wherein the angles range between 10 and 170 degrees.

In one embodiment, the present invention is a method of bone reduction using special screws having separable head and body sections to shift internal fixation to external fixation comprising: laying a bone reduction plate on a bone, fixing the bone reduction plate using crews of a first type wherein the first type comprises a type of screws comprising bodies and heads whose heads are unscrewable using a first wrench thereby forming an internal bone fixation and wherein, if desired, an external fixation is achieved by, unscrewing the head of the plurality of screws using the first wrench thereby allowing the bone reduction plate to detach from the bone leaving the bodies of the plurality of screws inside the bone, making a plurality of soft tissue holes in the soft tissue around the bone, passing the extension members through the soft tissue holes, attaching the extension members to the screw bodies inside the bone correspondingly and attaching the extension members to segments of an external modular plate, using cross pins to achieve a more stable fixation, thereby constructing an external frame for fixation of the bone.

In one embodiment, the present invention is a bone clamp for bone reduction comprising a clamp for holding a bone-plate assembly with a first arm and a second arm, wherein the first and second arms are pivotably movable against each other by applying a first force wherein at least one of first or second arms is a receiving arm which has an opening, a tool used for separating the soft tissue from the bone, wherein the tool comprising of a pad, a handle, and a second sliding mechanisms for position and orientation adjustments, wherein the receiving arm securely receives the handle of the tool.

In one embodiment, the opening has a first sliding mechanism to allow the handle of the tool to move along the receiving arm thereby mobilizing the handle to adjust the position of the tool.

In one embodiment, the present invention is a system for bone reduction for fixating bone fragments comprising: a modular main plate assembly system, the system comprising an array of plate segments with various dimensions and shapes and wherein a main plate is assembled using desired plate segments, the main plate securely affixed to a larger bone segment using screws, a twisted plate securely affixed at one end to the main plate and extended to attach using screws at the other end to a bone fragment at a location not generally aligned with and accessible to the main plate thereby stabilizing the bone fragment in a proper place.

In one embodiment, the twisted plate is curved for better reach to hard-to-access locations (e.g. a bone fragment to be fixed in a location not generally aligned or close to the main plate). In one embodiment, the twisted plate is connected to the main plate with adjustable angle between the twisted plate and the main plate. In one embodiment, the preceding system is used for fixation of fracture of the tuberosity of tibia.

In one embodiment, a system of bone reduction for fixating bone fragments comprising: at least one bone fragment and a bone part which is larger than the bone fragment wherein the bone fragment and the bone part are pieces from a fractured bone, a modular main plate assembly system comprising an array of plate segments with various dimensions and shapes and wherein an application-specific main plate is assembled using desired plate segments, the main plate securely affixed to the bone part using screws, a curved plate securely affixed at one end to the main plate and extended to attach using screws at the other end to the at least one bone fragment at a location not generally aligned with and accessible to the main plate thereby stabilizing the bone fragment in a proper place.

In one embodiment of the present invention, an angle between the twisted plate and the main plate is adjustable.

In one embodiment, the present invention is a system of bone fixation using bent plates comprising: constructing a fixation apparatus by connecting the bent plates using crews and positioning the fixation apparatus external to the patient's body, wherein the fixation apparatus uses pins under tension to enhance the stability and strength of the fixation apparatus wherein the bent plates are chosen and placed such that the distance between the bent plates and the body of the patient is minimized and the shape of the fixation apparatus customizingly conforms to the surface of the patient's body. In one embodiment, the present invention further comprises using rail plates externally and using a distractor compressor device in order to enhance bone union.

In one embodiment, a system for bone reduction comprising a bone, at least two bone clamps and at least one fixation plate, wherein the two bone clamps hold the bone and the plate, while holding the bone and the plate, the bone clamps are secured to be positioned each other in parallel eliminating their movement relative to each other in all directions.

In one embodiment, each of the bone clamps for holding a bone-plate assembly comprises a first arm and a second arm, wherein the first and second arms are pivotably movable against each other by applying a first force and wherein at least one of first or second arms is a receiving arm which has an opening on the body of the arm to securely receive a handle of a tool wherein the tool being used for separating the soft tissue from the bone, and the tool comprising of a pad, the handle, and a second sliding mechanisms for position and orientation adjustments. In one embodiment, the opening has a first sliding mechanism to allow the handle of the tool to move along the receiving arm thereby mobilizing the handle to adjust the position of the tool.

EXAMPLES

The following examples describe selected aspects and embodiments of the present teachings, including methods and apparatus for expanded bone fixation. These examples and the various features and aspects thereof are included for illustration and are not intended to define or limit the entire scope of the present teachings.

Example 1: CWP and Modular Plate with Spacers

The present article provides a system including method apparatus and kits for bone fixation with minimal detachment of soft tissue from bone with plate and CWP. The plate system includes a modular main plate and cylindrical spacer in different sizes and lengths that connects to the plate. As a result a distance C15, C16 from the bone is maintained. The optimal size of the spacer C19 is related to the planned distance between surface curve of the bone and interior surface of the plate in each part of the bone thereof. The desired space hence the length of the spacers may be not be equal. These spacers keep the plate in appropriate distance from the surface of bone without affecting the reduction. One advantage is that the need to detach soft tissue from the bone to put the plate on the bone C15, C16, E1, is eliminated. For fixation of the plate we use CWP with different diameters and sizes. Each CWP wing curved body includes a bone plate engagement portion, a bone fixation portion and an intercalating portion there between. The bone plate engagement portion includes a bottom surface and a top surface. The number of holes on each CWP is dependent on the size of CWP. One end of the curved wing plate attaches to the main plate that is placed over the reduced bone (E2 and E3). This main plate is affixed to the bone with two screws one in proximal part and one in the distal part of the fractured bone then this apparatus maintains the reduction until the CWP is placed over the plate.

On each part of fractured bone, at least three CWPs are placed on each side of the bone e3 in an alternative fashion and then the CWP is placed over the plate and affixed with locking screw. Because of the circular form of the CWP, the optimum fixation method for the most stability is achieved if the angle of direction of the screws with respect to each other becomes 90 degrees. The guide has two part: the tubular part enters the hole on the CWP and reaches the bone and a graduated part makes the angle of the screw with respect to the surface of plate 135 degree then we put another screw in other side of plate with the same angle and from another CWP to make the angle between two screws 90 degrees. Because of the circular form of the CWP, no parts of the CWP come far from the bone or make prominence maintaining an appropriate distance to the bone without a need to detach the soft tissue from the bone.

Because of the use of spacers in different sizes, we can use straight plate for bone with curved surface C15. Additionally or alternatively, the modular bone plate system is shaped as desired by connecting appropriate smaller plates together with the screws and therefore forming a plate parallel to the surface of bone C16. Then spacers of equal sizes are used to hold the plate a certain space apart from the bone. Each part of the modular plate has two ends. The thicknesses at two end sections of each part are reduced by removing material to form symmetrical steps. In other words, materials at the first and second end sections are removed from opposing sides such that a step at one end section and an inverted step at the second end sections are formed. Therefore, when assembling the parts of the modular plate, the step at one end fits and engages the inverted step at other end of the next part (see A1). The parts are then fixed with screw.

Because of round edges of A1, the parts can be rotated with respect to each other to achieve the desired position/orientation of the plate. Different lengths of the modular part are available to reach the desired direction and place for griping the screws and achieving appropriate lengths for the bone plate.

Sometime because of the shape of the fracture line, only weak portions or only one cortex of the cracked bone (instead of two cortexes) are located under the holes of the main bone plates. To overcome this issue, curved wings of proper length/shape are attached to the main plate to reach a more appropriate part of the bone for screw fixation (e.g. where two cortex griping can be achieved).

We can use this CWP for crossing the fracture line or crossing the weak part of bone that is not suitable for fixation. The CWP is used to cross the weak part of the bone and then the screw is inserted into the bone with adequate strength (F1). CWPs in different sizes and different curve angles can be used.

Overall the system may improve the functionally of bone plate to fix the bone in different sites and in variable distances to bone. The distance enables the operation without needs for detaching soft tissue from the bone and decreases the length of plate because of the increase in the footprint of the plate and contact bone. Another advantage is the viability of bone and power for union increase. Further, because of the distance between the plate and the bone, the chance of osteomyelitis decreases.

In one embodiment, the present invention presents a system for bone fixation comprising a plurality of curved wing plates (CWP) at least one modular main plate comprising a plurality of smaller plates with different sizes and round ends, wherein the plurality of smaller plates are rotatably connected to form the modular main plate, a plurality of cylindrical spacers wherein each of the plurality of curved wing plates comprising at least one bone plate engagement portion, at least one bone fixation portion and at least one intercalating portion, wherein the intercalating portion is positioned between the at least one bone plate engagement portion and the at least one bone fixation portion; wherein an array of holes are provided on each of the plurality of curved wing plates and the number of the holes in the array of holes is related to a size of the curved wing plate.

In one embodiment, the smaller plates are connected in desired directions to form the modular main plate and at least three CWP are positioned on each side of the at least one modular main plate and connected to the main plate using screws.

In one embodiment, the angle between two screws used on a CWP is 90 degrees. In one embodiment, straight modular plates are used along with spacers with different sizes whose lengths are related to a local separation distance between the straight modular plate and the surface of the bone.

In one embodiment, the present invention presents further using a modulated plate system comprising of a plurality of connected plates and a plurality of cylindrical spacers which are equal in length.

Example 2: Comminuted Bone Fractures—Use of Pins

Sometimes there is need to treat comminuted fractures containing small bone pieces. Frequently, these small bone pieces are not accessible from the main plate and we can fix them with pin and pin fixing CWP (B18, B19). This CWP has another superior movable part and a special hole at the end of it for securing the pin with superior movable part of CWP in the end hole and intermediate region that is spaced from the main plate to the exit site of pin from the bone.

FIG. 2 shows a pin-plate CWP for fixation of pin to plate. It includes two parts of handle B1 and intercalating portion B2, the edge of blade for fixation of pin B3 two large holes B4, adjacent smaller half circle holes B7, a number of lateral holes B5 for passage the extra pin, and hole for screw fixation of CWP to main plate. This CWP includes base part B18 and movable part B19. The movable part B19 is made from a thin sheet metal (e.g. steel) that provides the sheet with a degree of adjustability by allowing movement in a rail B15 located on the base part B18. The distance of blade fixating hole B8 to the handle of part B19 matches with the distance needed for receiving the blade to the point for fixation of pin in smaller hole B7 (brown line). Holes B4 at the end part of CWP have semi conical shapes. This shape of holes permits passage of the pin in different directions. Another mechanism for fixation of pin to plate is over the main plate. Each opening over the plate B20 has two parts of central big holes B21 and smaller side holes B22 suitable for passing the pins.

We can apply this type of CWP both before pinning and after pinning. If used after pinning, the end of pin is inserted into the exit site in the hole and then the other end is screwed to the main plate using a suitable hole on the main plate and then the upper movable part is pushed forward to the end part and related to the pin become engaged in each small hole the movable part trap in contact the pin and stop and then fix the movable part at the place with screw. These types of CWP are used for osteoporotic bone fixation. FIG. 4 shows the fixation of main plate to the bone with pins with no need for screws.

Example 3

Figure 8:
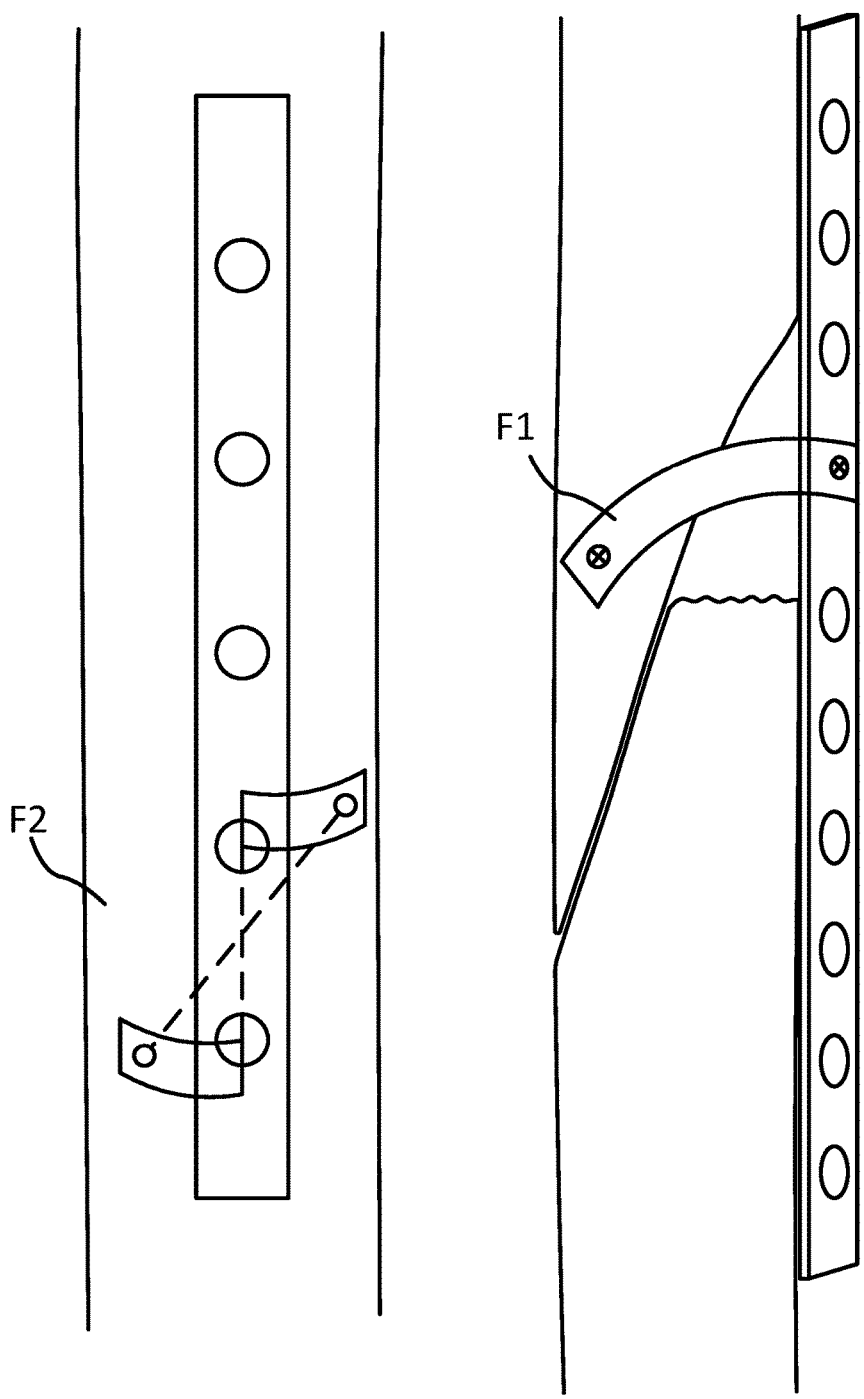
FIG. 8 shows the usage of curved wing tool to cross the comminuted or cracked part of bone for better fixation. By using the curved wing tool the distance between two screws increase that use for osteoporotic patient to reduce the chance of refracture.

In osteoporotic situations, because of insufficient bone mass, the screws do not demonstrate sufficient grip and the chance of re-fracture is high when the diameter of the hole made in the bone is high. The modular plate system of the present invention, in one embodiment is used for osteoporotic bone fixation. Using this system, we can have longer intervals between screws to reduce the number of holes and the stress in an osteoporotic bone and lower the chance of re-fracture (FIG. 8).

Another fixation method of fixation, namely the fixation of main plate to the bone with pins without the need for screws is shown in FIG. 4 for osteoporotic bones. For this purpose after reducing the fractured bone, the main plate is fixed to the bone with one screw in each side of plate. Then two pin-plate CWP are fixed onto the plate (one to each hole) with screws using the screw holes B6. Pins pass through the hole B5 over the CWP and two cross-pins pass from the hole B4 at the end of CWP and subsequently secured the pin in the smaller half circular hole B7 that is connected to the hole B4 (FIG. 2) and with blade of the movable part B19 (slide the blade in rail B118 over the part B18 and push the pin to the smaller hole B7, fix the upper part B19 on the lower part B18 by aligning appropriate holes as required by application, and fix the part using screws. Each hole B4 at the end part of CWP has a semi-conical shape. This shape of hole permits the pin to make different angles with respect to the hole. After fixation of pin in the distal hole, we use tension over the pin with tensioner B16 and then put the screw in the entrance hole B5 and fix the pin. Then the tensioner is opened and bent and the distal end of pin B17 is cut (FIG. 4).

As shown in FIG. 4, the CWPs is affixed beside each other in the same level B12 or different levels B13 relative to the direction of pin-pass. The cross pin pattern B14 (crossing the thickness of the bone) and the pins being under tension (tension fixation) increases the stability of the fixation and no screws are needed. This is specifically advantageous for the case of fixation of osteoporotic bones where the chance of plate detachment from the bone decreases comparing to the situation where screws are used.

Example 4: Articular Fixation with Two Plates

Sometimes in articular fracture (e.g. joint damage) comminuted bone parts are present which are too small for proper griping by screws and only very thin pins can pass through them. Sometimes because of the comminution of other part of articular fracture, proper stabilization is not achieved on the other side of the bone if stabilization is performed on one edge of bone only. In this situation it is advised that another plate be used on the other side and two plates be used. For this purpose, a frame for fixation of the contra lateral part of bone with the basement of the one plate is used on one side.

Figure 9:
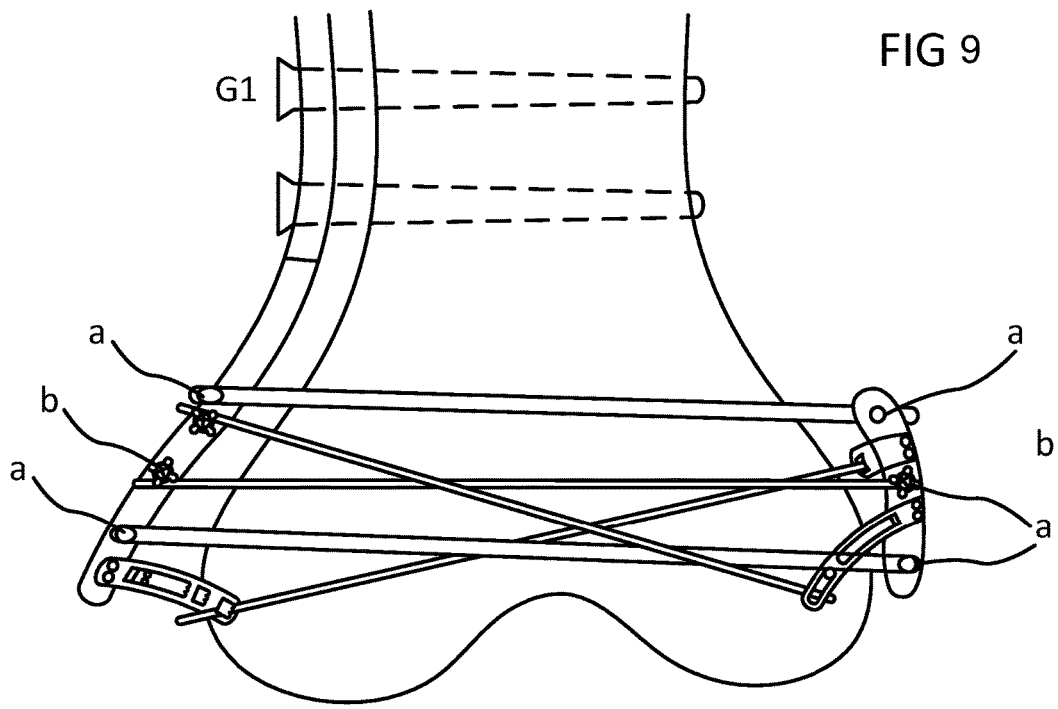
Figure 10:
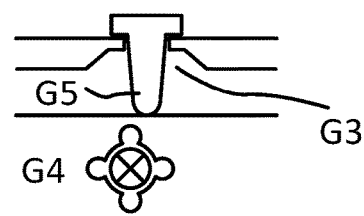
FIGS. 10-14 shows the usage of the system around the knee and constructing frame for intra-articular comminuted fracture for more stable fixation with pins to the plate in both sides of the joint with special curved wing increases the footprint of pin-plate.
Figure 11:
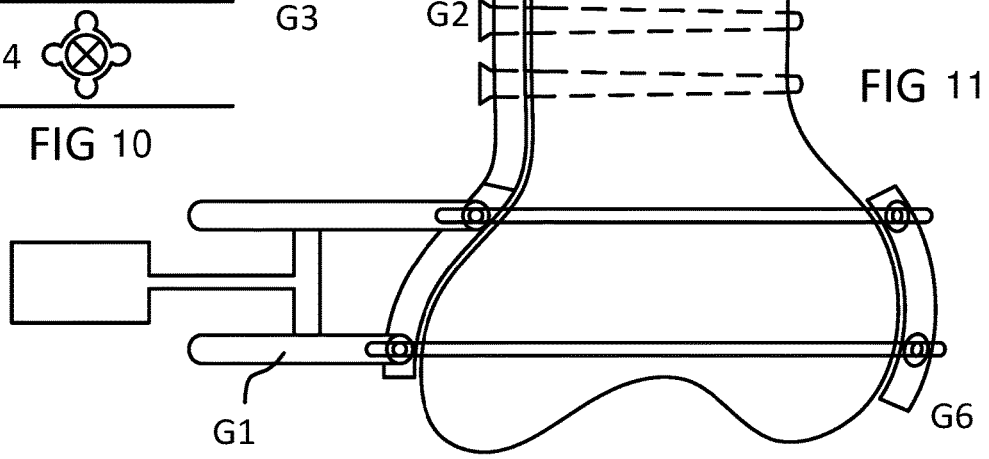
Figure 12:
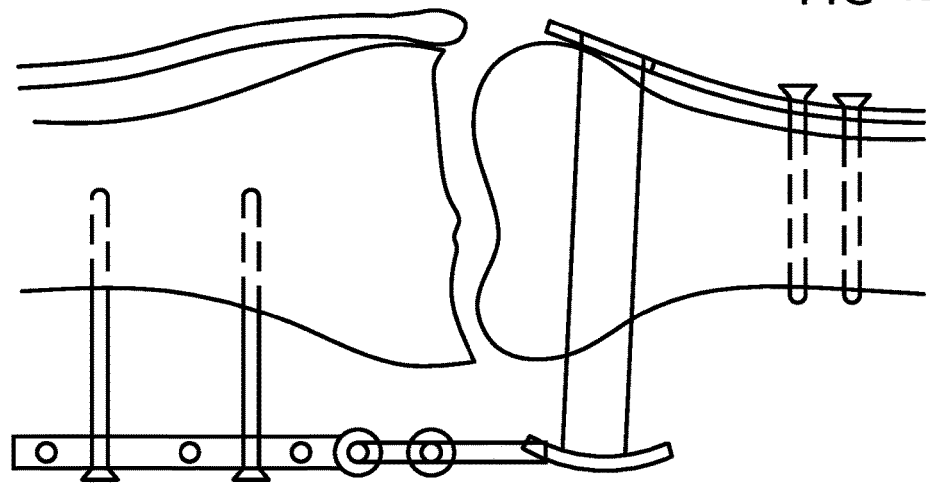
Figure 13:
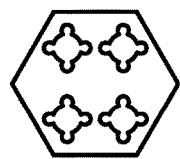
Figure 14:
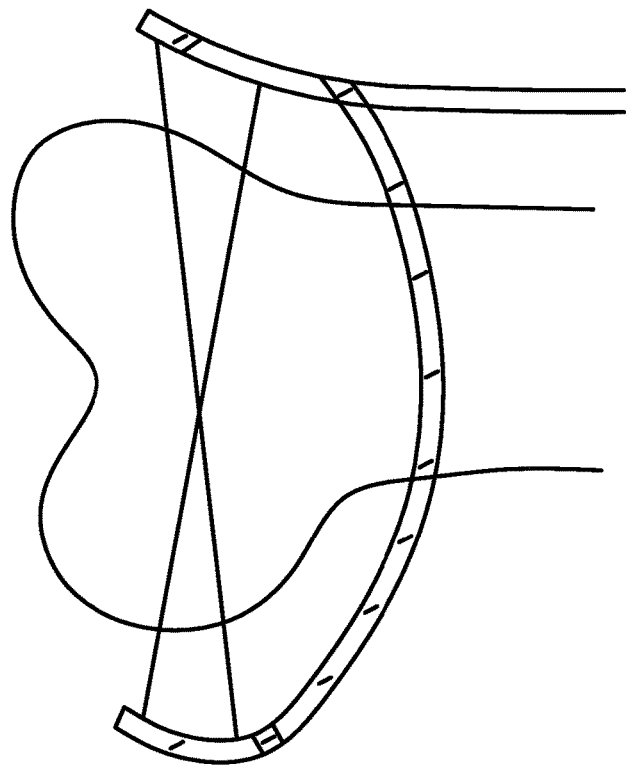

The following refers to FIGS. 9-14. After fixating the plate G2 over the bone in lateral side of distal femur, then the articular comminuted part is reduced and fixed with pin. Then we pass two 2.5 mm pins from the hole over the plate with guide G1 and this pin passes through some fractured parts and fixes them. Each hole over the plate has a special shape that makes the hole suitable for fixation of pin in the hole with screw (FIG. 10). Each hole set shown in FIG. 10 has one main hole G3, which has a wide opening for free movement of the pin enabling entrance into the hole in different directions, and 4 smaller holes G4 which are connected to the main hole G3. After passage of the pin from the hole, we put a screw with a wedge-shaped tip in the hole, pull and translate the pin in order to position the pin in the nearest smaller hole G4 and then fasten the screw. The screw then tightens the pin in the hole G4. Properly sized screws must be used for tightening the pin in the plate's hole depending on the pin's thickness. On the other side we put a CWP G6 over the two parallel pins that pass from the bone. Now we can use tension over the pin and while under tension we tighten a suitable screw and fix it in the hole in a fashion similar to the hole on the main plate. Now we can use the frame in FIG. 11 for passage of other pins and fixing them on this frame (FIG. 9). We can use wings in different direction for adding other pins in order to increase stability of fixation of other small comminuted fractured parts.

Figure 17:
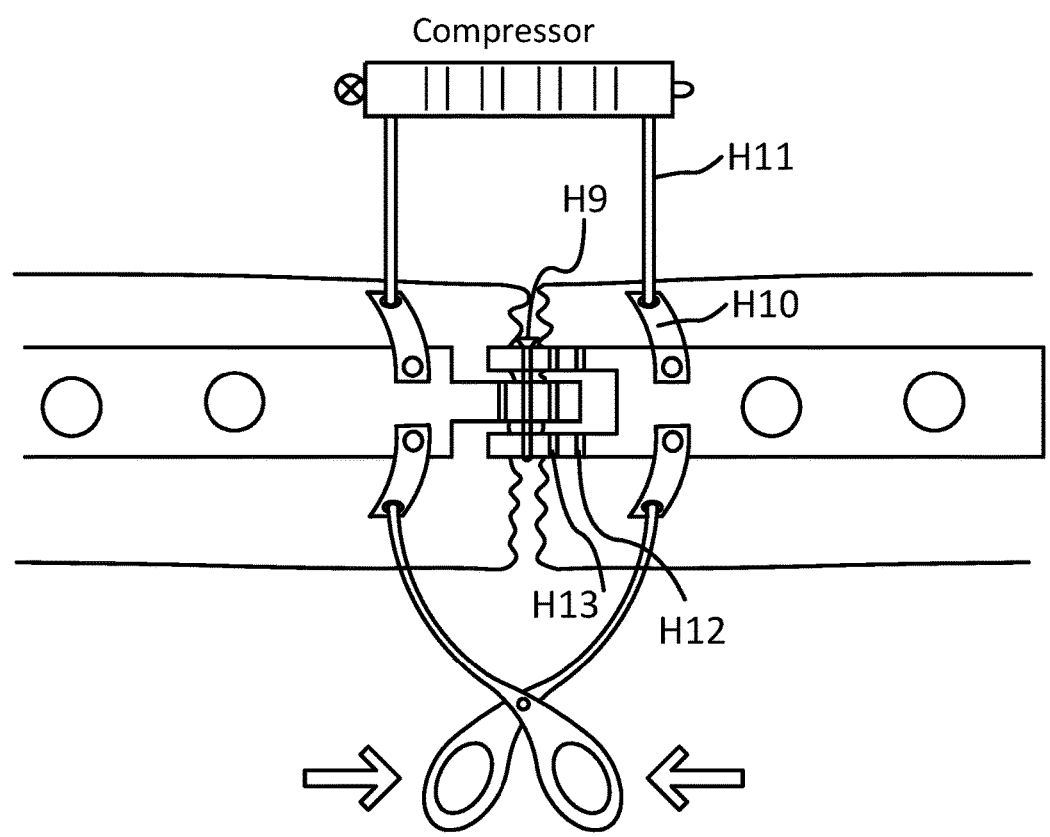

We can use this structure as external fixator outside the body and two plate located outside of skin and the main plate fix to the bone with long screw cross the screw and put the plate outside the skin and then after fixation of plate to the bone pass the two parallel pin and on the other side pass the pin through the skin and put CWP on the pin outside the skin and fix the pin to the CWP. Also this method is flexible and we can put CWP beneath the skin and then only in lateral border of the knee the plate are outside the skin. Another method we can put the main plate in lateral side over the bone and put medial CWP outside the skin without need to incise the skin in medial side. CWP has special shape and size for each joint and the goal is to reach a suitable surface for fixation of pin and increase the stability FIG. 13. for more stability on the medial side we can attach the CWP with a hinge to the another plate that we put it on the medial side of tibia and this plate work as a base for increasing the stability FIG. 12 or if the lateral plate is outside of the skin and the CWP in medial is outside the skin we can attach them with semi-circular half plate part that G7 connect these two part outside the knee Example 5: Rail Plate Sometimes after the fixation of the plate, a gap remains between the bone segments in the fracture site. To fix the problem, one needs to loosen the screw(s) of the plate, change the location of hole and then fasten again sometimes using higher compression force). In one embodiment of the present invention, we compress the fracture site with rail plate in order to eliminate the gap (FIGS. 15-17).

For example, rail plate fix in 3 mm distance in rail part. The conical/wedge shaped hole and the screw allows movement of the part Ha to part Hb step by step in 1.5 mm length.

After fixation of the fractured bone, if a gap exists between the pieces of the fractured bone, we open the screw H6 and then compress toward each other the two fractured bone part Ha and Hb, position conically shaped wedge H7 with holder H8 and push it through the hole H1 until it enters the hole H2. Using this method, part Hb is pulled toward part Ha for 1.5 mm and the screw fixating hole H5 is aligned (FIG. 16).

In one embodiment, if more repositioning is needed, we use another screw H9 in the hole H3, after only the tip of the screw enters the hole H4, we push back the screw H7 from the hole H1, insert H9 in the hole H4 completely and then part Hb with the fractured bone attached to it moves another 1.5 mm towards part Ha (which is attached to the other piece of the fractured bone). Now the screw hole H6 is aligned and we can use a screw and fix the rail in the new position. This way, a displacement of 3 mm is achieved. The 1.5 mm interval is an example and to have more options we can change the number of screws and holes and the primary intervals of the rail plate.

Another application of this system is perfecting the union by compression at the fracture region without removal of the plate. As shown in FIG. 17, after refreshing the edge of non-union fracture bone, two CWPs are attached in each side of the plate and in both fracture sites H10. Two compression devices are positioned on both sides H11, then remove the fixating screw of rail and conical shaped wedge H9 and compress the nonunion part of fractured bone. After compression we use the conical shape wedge in the new position prepared H12, 13. Then the rail is affixed in the new position. This way we can compress the fractured bone without removal of the plate.

Example 6

The fixation of fractures involving tuberosity of tibia when accompanied with the fracture of proximal tibia is complex because the main structure of the bone has been destroyed. However, in one embodiment of the present invention, good stability is achieved after reduction of proximal tibia with plate the tuberosity remain detached (FIG. 5).

In this embodiment, we can fix the tuberosity with the main plate. Each twisted modular plate has two parts C1 and C2 with one hole. One skilled in the art recognizes that the number of holes and the degree of rotation of these sheets with respect to each other can be altered per application. For example in distal radius we need 90 degree in one location as in C3 and 110 degree in another location as in C4 (e.g. A226, A27). Each hole has four smaller holes on the periphery and attached to the main hole C6. Sometimes the tuberosity or every detached parts of the bone are not only not accessible from the main plate but also so small and comminuted that we need to fixate them with pins. For this purpose, after fixating the proximal tibia fracture and positioning and fixing the plate in lateral side C8 we add a twisted modular plate (TMP) to the hole near the tuberosity C5 and a TMP connect to the main plate and then part C2 of TMP lies over the tuberosity. Now we pass a pin and this pin engages the tuberosity and then put a screw C7 in the hole this screw pulls the pin into the smaller hole and then bends the end of the pin outside the plate and the head of the screw draws over the bend part. The pin is fixed in the hole C10. The hole on the TMP has a semi conical shape and this pattern permit the pin pass the hole in multidirectional pathway C9.

Example 7: Conversion of Internal Fixation to External Fixation

Figure 7:
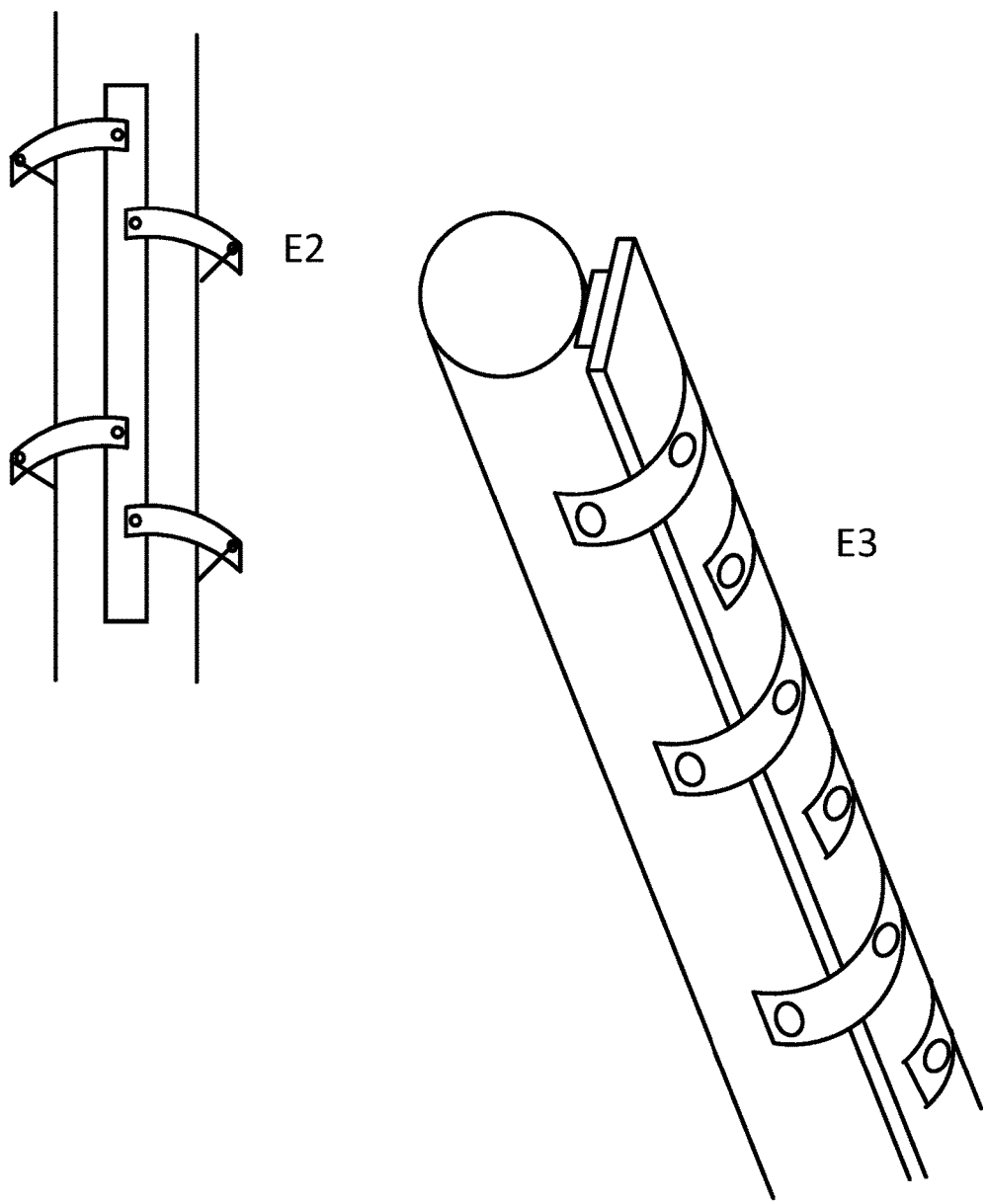
FIG. 7 shows the method of fixation of the bone to use short length plate instead of long plate by using the curved wing for fixation and the angle of the pin or screw fastener with respect to each other and use of guide to achieve this direction.

In the case of infection, currently one of the best options is removing the plate from the bone and instead using external fixator outside the skin. For this, after removing the screw, the plate is detached from the bone and then new holes are created on the bone to fixate the bone with external fixator using a new Schanz screw. The Schanz screw has a diameter of about 5 mm with threaded tapered tip. By using the modular bone plate in one embodiment of this invention we can change the internal fixation to external fixation with minimal rework and intervention. After fixing the plate and using 90 degrees CWP on both sides (FIG. 7, E2-3), we can then open the head of screw A21, remove the plate and leave the body of screw in the bone. Now the long body is attached to the screws with extension A25. Then we attach the extension members to the modular plate outside the skin and make a frame outside the body for fixation of the infected bone. With the use of these screws and the long wings while maintaining the main plate outside the skin, good stability can be achieved, because the direction angle between two screws is 90. Additionally we can attach longer half circle curve wing and some cross pins to get more stable fixation.

Figure 18:
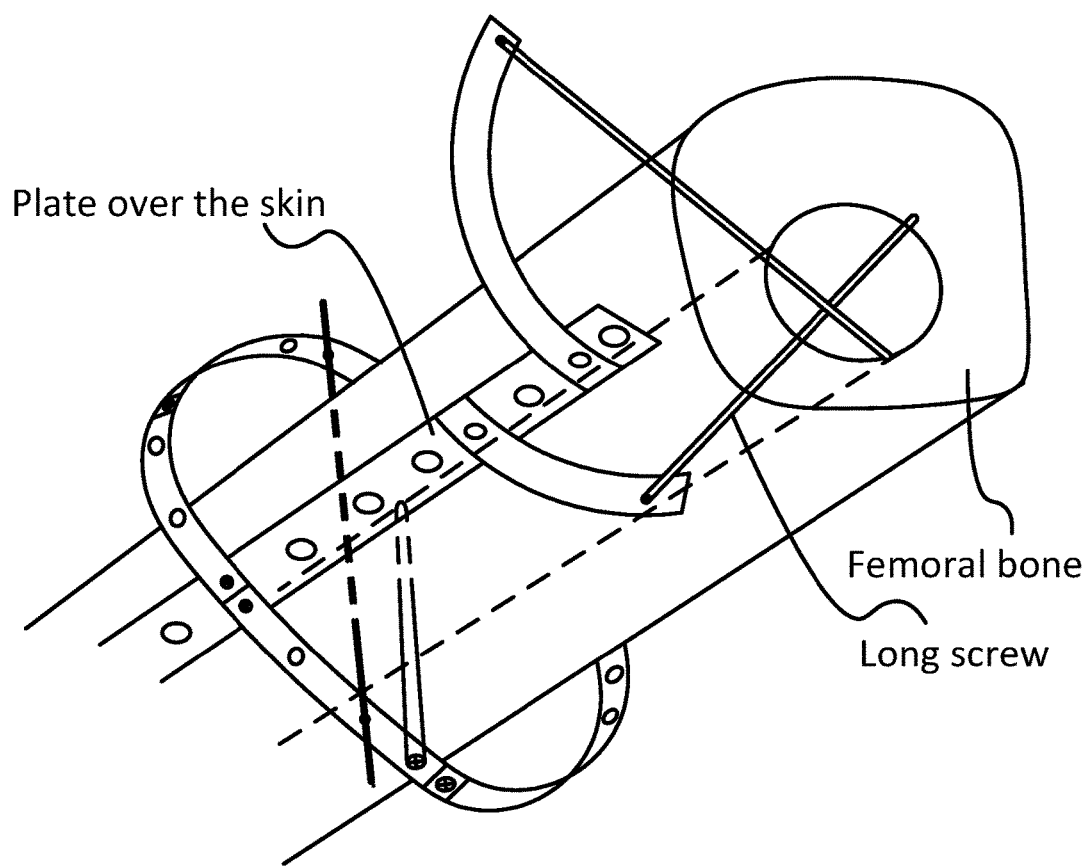
FIGS. 18 and 19. show the method for external fixation apparatus. Modules of part-circular plates are assembled as needed. Pins are added to the frame and connected to the plate for more stable fixation. This method of making the modulated external fixation apparatus using part-circular or oval-shaped modules, are constructed so that the apparatus more perfectly conform to the limb's surface hence making the apparatus more tolerable by the patient.

FIG. 18 shows the use of modular plate outside the skin. Using screws of internal fixation, it is possible to attach pins cross the bone to the modular plate out of the skin with the pin-plate CWP of FIG. 2 outside the body or the smaller hole in the opening on the plates B21, 22, 23, 24.

In the case of external fixation usage, other plates can be attached parallel to the first plate and connected with each other with curved plates which are positioned horizontally. Therefore, higher stability is gained using this type of frame (JB, JA).

Using the embodiments of this invention, the external fixator can be assembled such that the general shape of the final fixator conforms to the shape of the organ. We can use wings with differently angled curves to bring the fixation plate sufficiently near the skin in whole or part of the organ as desired. For example, around the thigh area, the external parts of the fixation can be placed near the skin. This helps the device more tolerable for the patient.

Along the fracture line we put straight rail plate JB1 and attach distal and proximal part of frame with these rail plates and fix the rail with a distractor compressor device. The bone parts are compressed against each other to achieve better union using CWPs in different sizes and curves.

Figure 19:
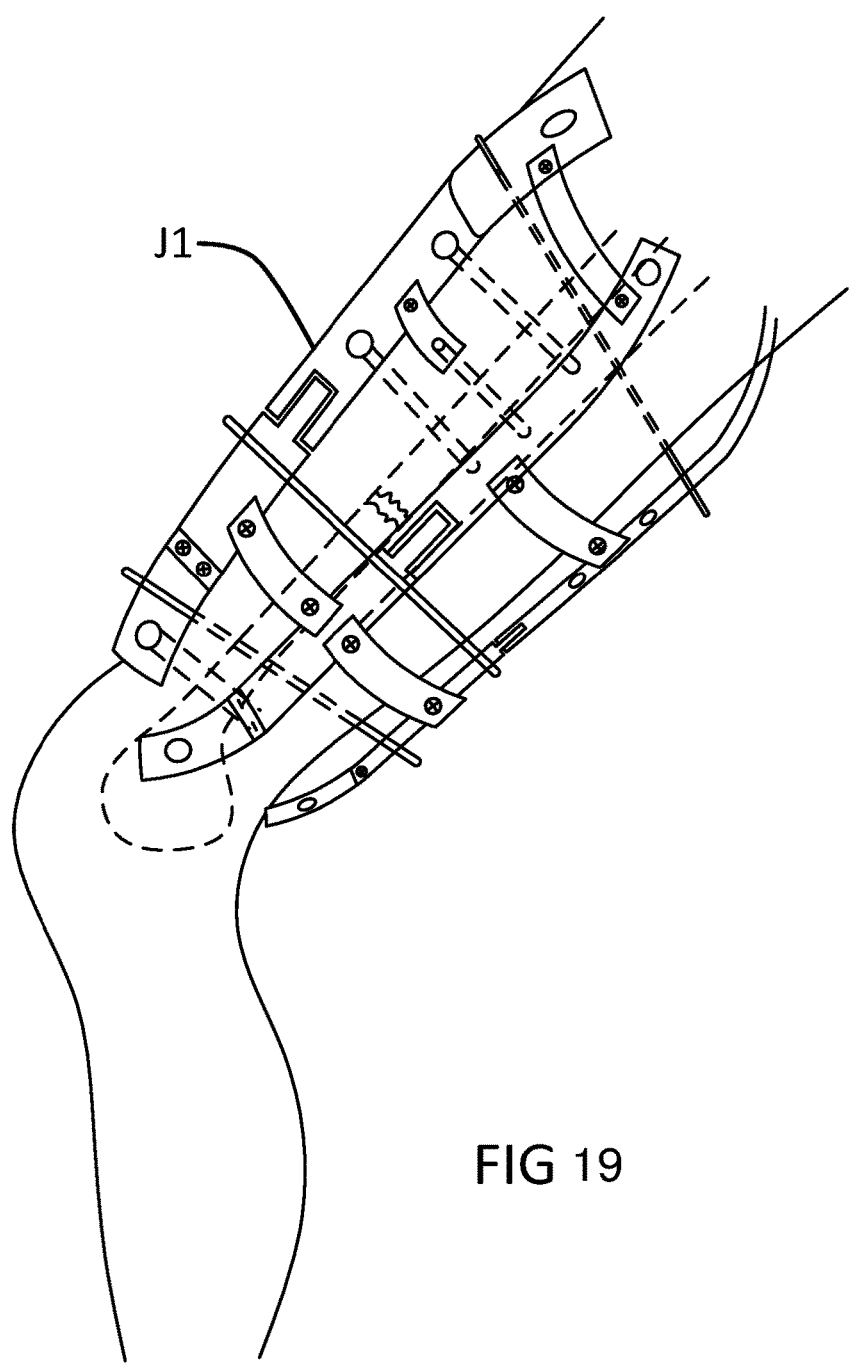
Figure 20:
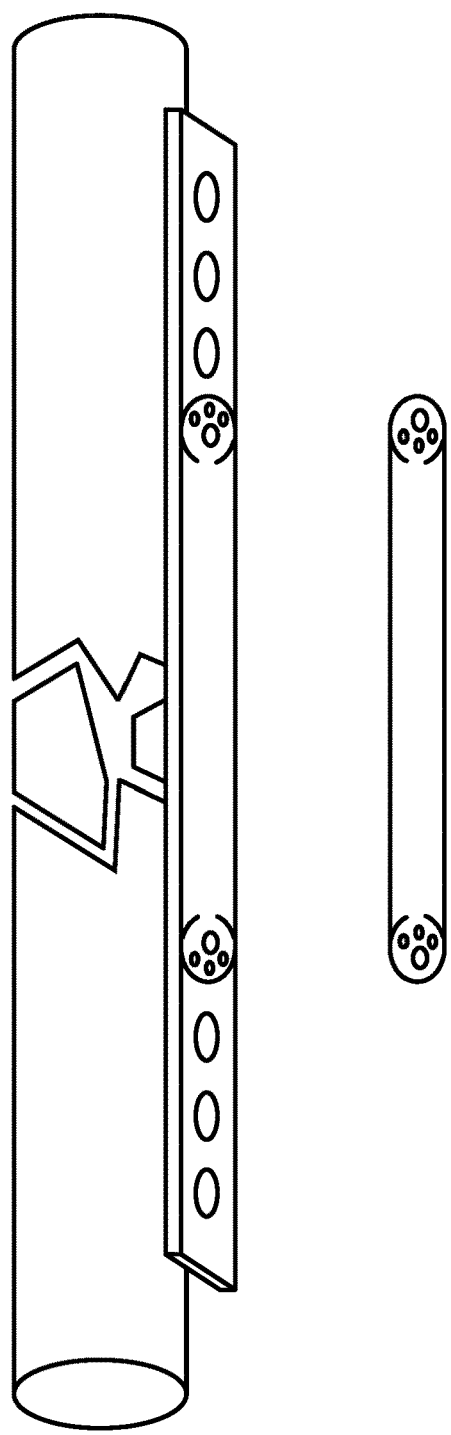
FIG. 20 illustrates an application of the present invention in reducing bones. The main plate is hingedly connected to distal and proximal plates which are connected to the bone segments using screws. The angle of connection is adjustable and is fixable after adjustment using e.g. pins or screws.

FIG. 19 shows CWP near the joint use to make the external fixator close to the skin therefore the external fixator becomes more tolerable for the patient.

When we use regular bone clamp to hold two parts of fractured bone near each other we don't have enough space to put the plate on the bone and change the position of plate to reach a good contact and we should hold two parts of fractured bone near each other vigorously. in this system we planned special plate part and change in the regular clamps for easier reach to good reduction.

Figure 21:
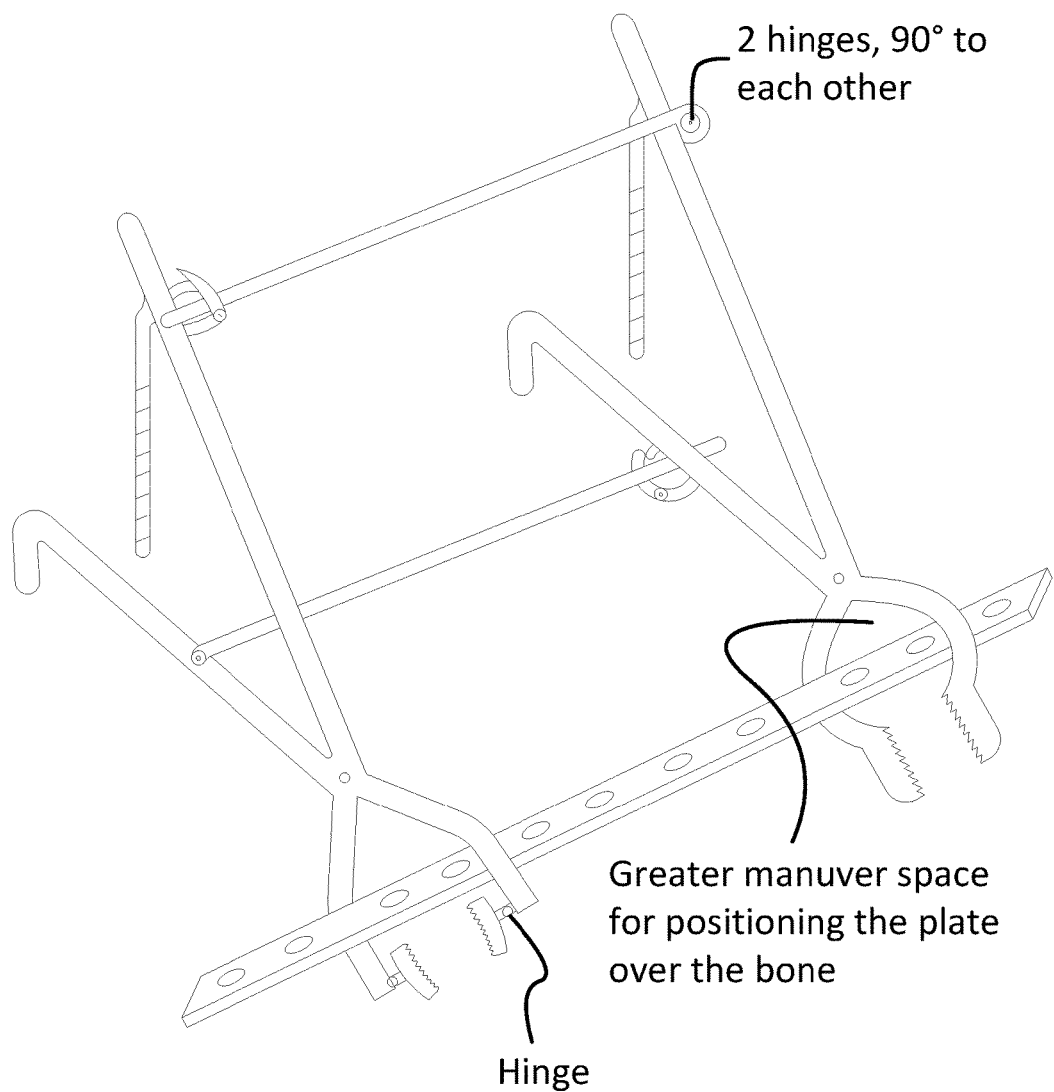
FIG. 21 shows a system of bone reduction using two bone clamps which are connected to each other such that the plane of the bone clamps stay parallel.
Figure 22:
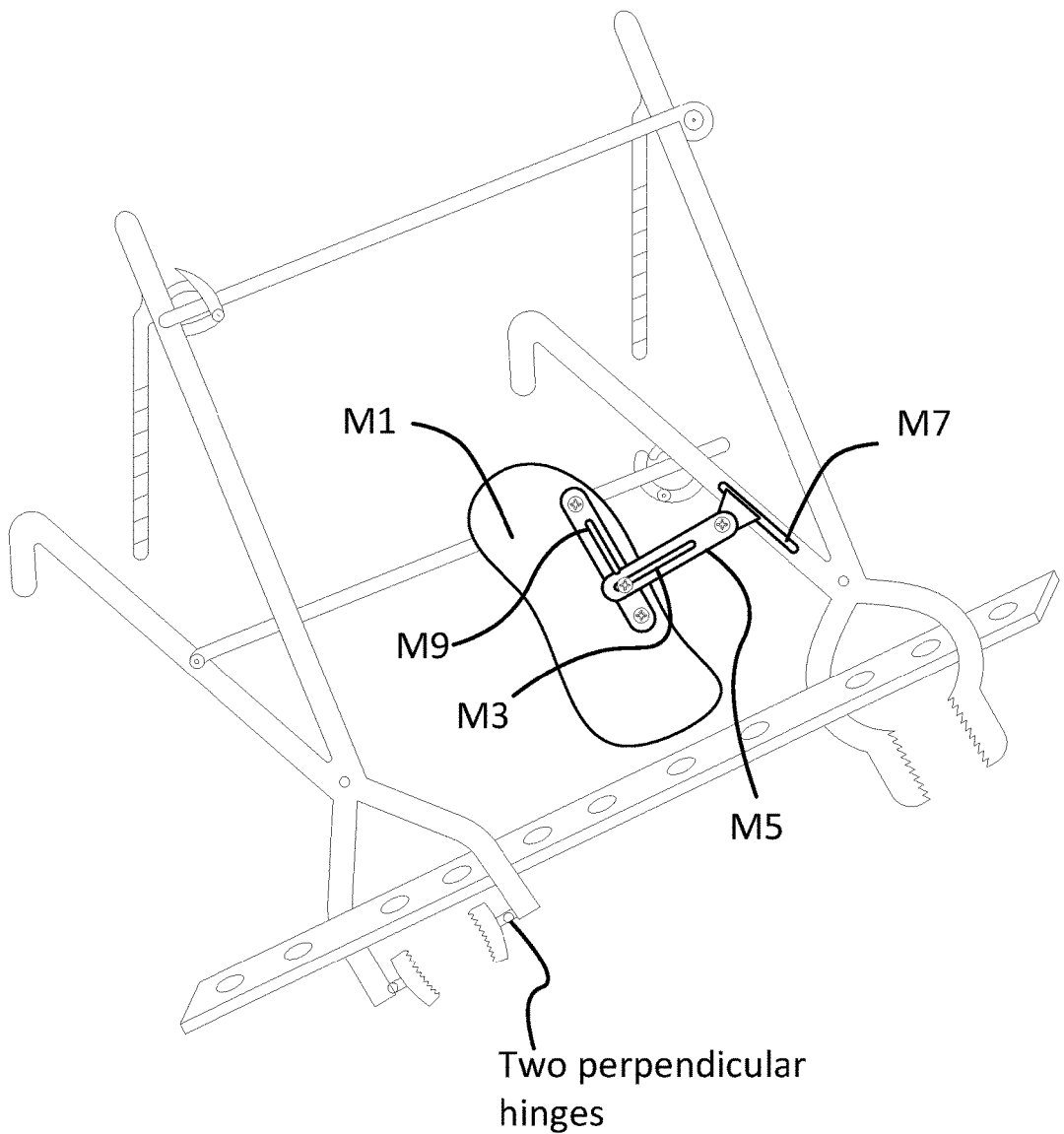
FIG. 22 shows a system of bone reduction using two clamps that includes built-in Bennett for temporarily separating soft tissue from the bone.

For easier fixation we have modified the lane bone clamps. Circular space between two blades are opened up enough to allow a plate pass through circular space easily without opening the clamps and also the circular part of blade work as a retractor to the muscle around the bone to make good exposure. An external hinged rod will be fixating the two clamps together so the fracture site is fixed and the plate can be placed on the bone easily. Two types of clamps are show in FIGS. 21 and 22. On the handle of bone clamp we connect the rod to handle with two hinges in 90 degree angle direction to form a universal joint. These connections permit moving the hinges to achieve better reduction after closing the rod to the other bone clamp.

In one embodiment, a bone clamps are equipped with a Bennett M1 (FIG. 22) connected thereto. The blade of Bennett M1 is connected to a handle of one clamp (FIG. 22) or both clamps (not shown) in the assembly using a rod M5. The rod M5 is equipped with an adjusting apparatus with a rail M3 to adjust the distance between the Bennett and the clamp handle. The position of the Bennett relative to the claims is further adjustable by using the rail systems M7 and M9. Therefore, when clamps are being positioned to properly grip the bone and plate, the soft tissue is conveniently raised or separated from the bone at the same time by merely moving the handle of the bone clamp. This improves the time efficiency and boosts the success rate of the surgery.

Any variations of the above teachings are also intended to be covered by this patent application.

The invention claimed is:

1. A system for perfecting bone contact in bone fixation by compressing the bone parts against each other and moving them a total bone displacement distance, comprising:

a rail comprising a fork with an elongated handle, said handle having a first plurality of holes thereon for fastening to a first part of a fractured bone, said fork comprising two parallel plates connected to said elongated handle, positioned a first distance apart, and a second plate with a proximal and a distal end, wherein the distal end comprises a second plurality of holes for fastening to a second part of said fractured bone;

wherein said parallel plates of said fork define a first extended region configured to extend outward from a first fractured edge of said first part of said fractured bone, and said second plate defines a proximal extended region configured to extend outward from a second fractured edge of said second part of said fractured bone when the rail and the second plate are affixed to said first and second parts of said fractured bone;

said parallel plates of said fork comprising a first plurality of conically-shaped holes which are identical and aligned relative to one another, such that said holes are spaced a first pitch apart, and said second plate comprising a second plurality of conically-shaped holes spaced a second pitch apart, wherein the first pitch is different from the second pitch;

wherein the width of said proximal extended region of said second plate is less than said first distance for allowing insertion of the second plate between said two parallel plates of said fork;

wherein said second plate is configured to be slidably positioned between said two parallel plates of said fork such that said first extended region and second extended regions at least partially overlap, allowing said first part and said second part of said fractured bone to be moved toward each other;

wherein said overlapping is performed by creating a desired alignment position, comprising aligning said fork with said second plate such that at least one of said first plurality of conically-shaped holes, that is a first target hole, is offset with at least one of said second plurality of conically-shaped holes, that is a second target hole, and the offset results in an amount that is equal to or a fraction of said total bone displacement distance needed; and a plurality of conically shaped wedges, wherein a first conically shaped wedge of said plurality of conically shaped wedges is passed through said first target hole and pushed toward insertion into said second target hole such that said offset is eliminated by pushing said second bone part toward said first bone part.

2. The system of claim 1, comprising after eliminating said first offset, the process is similarly repeated by inserting another conically shaped wedge into another one of conically shaped holes to eliminate a second offset.

3. The system of claim 2, wherein said first offset and said second offset are between 0.5 mm and 10 mm each.

4. The system of claim 1, wherein said first offset is between 0.6 mm and 10 mm.

5. The system of claim 1, wherein said fork is configured to be fastened to a first piece in a first customizable main plate at a location on its elongated handle and the second plate is further configured to be fastened to a second piece in a second customizable main plate at a location on its distal end, wherein said first and second customizable main plates are configured to be fastened to said first and second bone parts, respectively.

6. The system of claim 5, wherein when fastened, each one of said fork and said second plate creates an angle between 0 and 90 degrees with said first and second pieces in corresponding customizable main plate systems.

7. The system of claim 6, wherein the elongated handle of said fork and the distal end of said second plate comprise at least three adjustment holes for fixing said angles to stay between 0 and 90 degrees by inserting pins or screws in said adjustment holes.

8. The system of claim 5, wherein said fork and said second plate form a rail-plate structure and said first and second pieces are connected to the two ends of the rail-plate thereby one connecting to the elongated handle of the fork and the other connecting to the distal end of the second plate, wherein at least one of said first and second pieces include two opposite recesses made in its mid-section.

9. The system of claim 8, wherein a bone clamp is further used to hold a bone-main plate assembly and arms of said bone clamp are placed at the recesses to thereby hold the bone-main plate assembly.

10. The system of claim 9, wherein said arms of said bone clamp are curved to allow for extra space for placing said customizable main plate on first and second parts of said fractured bone while being held by said bone clamp.

* * * * *